United States Patent [19]
Lai et al.

[11] Patent Number: 5,206,154
[45] Date of Patent: Apr. 27, 1993

[54] METHOD OF PRODUCING CECROPINS BY MICROBIOLOGICAL TECHNIQUES

[75] Inventors: Jiunu Lai; Jar-How Lee, both of Los Angeles; Yun-Long Lin, Los Angeles; Dan Ray, Encino; Gary Wilcox, Malibu, all of Calif.

[73] Assignee: Xoma Corporation, Berkeley, Calif.

[21] Appl. No.: 637,199

[22] Filed: Jan. 3, 1991

Related U.S. Application Data

[60] Division of Ser. No. 474,304, Feb. 5, 1990, Pat. No. 5,028,530, which is a continuation-in-part of Ser. No. 645,309, Jan. 28, 1985, abandoned.

[51] Int. Cl.$^5$ ..................... C07K 13/00; C17N 15/62; C17N 15/63
[52] U.S. Cl. ................. 435/69.7; 435/252.3; 435/320.1; 530/350
[58] Field of Search ................. 435/69.7, 252.3, 320.1; 536/27; 530/350

[56] References Cited

U.S. PATENT DOCUMENTS

| | | | |
|---|---|---|---|
| 4,332,892 | 6/1982 | Ptashne et al. | 435/68 |
| 4,355,104 | 10/1982 | Hultmark et al. | 435/70 |
| 4,366,246 | 12/1982 | Riggs | 435/68 |
| 4,520,016 | 5/1985 | Hultmark et al. | 514/12 |

FOREIGN PATENT DOCUMENTS

WO8501746 4/1985 PCT Int'l Appl. .
2084584 10/1990 United Kingdom .

OTHER PUBLICATIONS

Rüther, U. et al., *The EMBO Journal*, 2(10):1791–1794 (1983).
Heusterspreute M. et al., *DNA*, 3(5):377–386 (1984).
Gibbs, J. B. et al., *Proc. Natl. Acad. Sci. USA*, 81:5704–5708 (1984).
Reiss, B. et al., *The EMBO Journal*, 3(10):3317–3322 (1984).
Hedge, P. J. et al., *FEBS Lett.*, 176(1):179–184 (1984).
Bomen et al., *Current Topics Microbiol. Imun.* 94–95:-75–91 (1981).
Steiner et al., *Nature* 292:246–248 (1981).
Qu et al., *Eur. J. Biochem.* 127:219–224 (1982).
Hultmark et al., *Eur. J. Biochem.* 127:207–217 (1982).
Andreu et al., *Proc. Natl. Acad. Sci. USA* 80:6475–6479 (1983).
Johnson et al., *Gene* 34:137–145 (1985).
Hoftsten et al., *Proc. Natl. Acad. Sci. USA* 82:2240–2243 (1985).
Hurt, E. C. et al., *The EMBO Journal* 3(B):3149–3156.

*Primary Examiner*—Robert J. Hill, Jr.
*Assistant Examiner*—John D. Ulm
*Attorney, Agent, or Firm*—Sterne, Kessler, Goldstein & Fox

[57] ABSTRACT

A polynucleotide molecule expressible in a given host comprising the sequence of the araB promoter operably linked to a gene which is heterologous to said host. The heterologous gene codes for a peptide that is biologically active. The invention also relates to a genetic construct which comprises a first genetic sequence coding for cecropin operably linked to a second genetic sequence coding for a polypeptide which is capable of suppressing the bactericidal effect of the resulting fusion protein towards an otherwise cecropin sensitive bacterium.

15 Claims, 12 Drawing Sheets

FIG. 7

METHOD OF PRODUCING CECROPINS BY MICROBIOLOGICAL TECHNIQUES

RELATED APPLICATION

This application is a division of application Ser. No. 07/474,304 now U.S. Pat. No. 5,028,530, filed Feb. 5, 1990, which is a continuation in part of application Ser. No. 07/645,309, filed Jan. 25, 1985, which is now abandoned.

BACKGROUND OF THE INVENTION

1. Field of The Invention

The present invention relates to the field of recombinant DNA technology and to the use of araB promoters in the expression of heterologous genes in transformed hosts. This patent also relates to the design, cloning and expression of genes coding for the bactericidal peptide cecropin and analogues thereof.

2. Brief Description of The Background Art

Genetic information, encoded in DNA molecules, is expressed by a series of steps involving transcription of the DNA into mRNA and the subsequent translation of the mRNA into polypeptides or proteins. The expression of the encoded information to form polypeptides is initiated at the promoter site, a region on the DNA molecule to which RNA polymerase binds and initiates transcription. Promoters that have been used in recombinant DNA methods for expressing heterologous genes include the beta-lactamase (penicillinase) and lactose (beta-galactosidase) promoter systems (Change et al., *Nature*, 275: 615 (1978); Itakura et al., *Science*, 198: 1056 (1977); Goeddel et al., *Nature*, 281: 544 (1979)) and tryptophan (trp) promoter system (Goeddel et al., *Nucleic Acids Res.*, 8: 4057 (1980); EPO Application Publication No. 0036776). Other known promoters include the bacteriophage lambda promoters, ($P_L$) and ($P_R$), hut, colicin $E_1$, galactose, alkaline phosphatase, xylose A, and tac.

The araB gene and its promoter (araB) are located in the L-arabinose operon. The L-arabinose operon (araBAD) in *Escherichia coli* and in *Salmonella typhimurium* has been studied. Of particular interest is the L-arabinose operon in *S. typhimurium*; its sequence is described in Horwitz, A. et al., "DNA Sequence of the araBAD-araC Controlling Region in *Salmonella typhimurium* LT2," *Gene*, 14: 309-319 (1981), Lin, H.-C. et al., "The araBAD operon of *Samonella Typhimurium* LT2, I. Nucleotide Sequence of araB and Primary Structure of Its Product, Ribulokinase," *Gene*, 34: 111-122 (1985); II. "Nucleotide Sequence of araA and Primary Structure of Its Product, L-Arabinose Isomerase," *Gene*, 34: 123-128 (1985; III. "Nucleotide Sequence of araD and Its Flanking Regions, and Primary Structure of its Product, L-Ribulose-5-Phosphate-4-Epimerase," *Gene*, 34: 129-134 (1985). The araBAD operon contains three structural genes which are responsible for the initial metabolism of L-arabinose. Lee, Jar-How et al., "Genetic Characterization of *Salmonella typhimurium* LT2 ara Mutations," *J. of Bacteriology*, 158: 344-46 (1984). L-arabinose is first converted into L-ribulose by the araA gene product, L-arabinose isomerase. L-ribulose is then phosphorylated to L-ribulose-5-phosphate by the araB gene product, ribulokinase. The araD gene product, L-ribulose-5-phosphate 4-epimerase, catalyzes the conversion of L-ribulose-5-phosphate to D-xylose-5-phosphate which then enters the pentose phosphate pathway. The araBAD operon is coordinately controlled by the inducer L-arabinose and the araC regulatory gene product.

Since, in one embodiment of the invention disclosed and claimed herein, the araB promoter is operably linked to the gene coding for cecropin and inserted into a suitable host for expression of the cecropin protein, it is worthwhile to review background references on cecropins.

The immune system of the Cecropia moth and several lepidopteran insects is characterized by an effective humoral response which is mainly associated with the cecropins, a recently discovered family of antibacterial peptides (Boman, H. G. and Steiner, H., *Current Topics In Microbiology And Immunology*, 94/95: 75-91 (1981)). Three major cecropins, A, B and D, have been purified from immune hemolymph and their sequences have been elucidated (Steiner, et al., *Nature*, 292: 246-248 (1981); Qu, et al., *European Journal of Biochemistry*, 127: 219-224 (1982)l; Hultmark, D., Ibid, 127: 207-217 (1982); and Hultmark, U.S. Pat. No. 4,355,104). All cecropins are small basic peptides with a high degree of mutual sequence homology. The amino acid sequences of cecropins B and D from *Antheraea pernyi* (A.p.) and from *Hylophora cecropia* (H.c.) are as follows:

| | 1 | 5 | 10 |
|---|---|---|---|
| A.p. Cecropin B | H₂N—Lys—Trp—Lys—Ile—Phe—Lys—Lys—Ile—Glu—Lys—Val—Gly—Arg— | | |
| H.c. Cecropin B | H₂N—Lys—Trp—Lys—Val—Phe—Lys—Lys—Ile—Glu—Lys—Met—Gly—Arg— | | |
| H.c. Cecropin A | H₂N—Lys—Trp—Lys—Leu—Phe—Lys—Lys—Ile—Glu—Lys—Val—Gly—Gln— | | |
| H.c. Cecropin D | H₂N—Trp—Asn—Pro—Phe—Lys—Glu—Leu—Glu—Lys—Val—Gly—Gln— | | |
| H.c. Cecropin D | H₂N—Trp—Asn—Pro—Phe—Lys—Glu—Leu—Glu—Arg—Ala—Gly—Gln— | | |
| | 15 | 20 | 25 |
| A.p. Cecropin B | Asn—Ile—Arg—Asn—Gly—Ile—Ile—Lys—Ala—Gly—Pro—Ala—Val—Ala— | | |
| H.c. Cecropin B | Asn—Ile—Arg—Asn—Gly—Ile—Val—Lys—Ala—Gly—Pro—Ala—Ile—Ala— | | |
| H.c. Cecropin A | Asn—Ile—Arg—Asp—Gly—Ile—Ile—Lys—Ala—Gly—Pro—Ala—Val—Ala— | | |
| H.c. Cecropin D | Asn—Ile—Arg—Asn—Ala—Val—Ile—Ser—Ala—Gly—Pro—Ala—Val—Ala— | | |
| H.c. Cecropin D | Asn—Ile—Arg—Asp—Gly—Ile—Ile—Ser—Ala—Gly—Pro—Ala—Val—Ala— | | |
| | 30 | 35 | |
| A.p. Cecropin B | Val—Leu—Gly—Glu—Ala—Unknown C-terminal | | |

-continued

H.c. Cecropin B  Val—Leu—Gly—Glu—Ala—Lys—Ala—Ile—Leu—Ser—CO—R

H.c. Cecropin A  Val—Val—Gly—Gln—Ala—Thr—Gln—Ile—Ala—Lys—CO—R

H.c. Cecropin D  Thr—Val—Ala—Gln—Ala—Thr—Ala—Leu—Ala—Lys—CO—R

H.c. Cecropin D  Thr—Val—Ala—Gln—Ala—Thr—Ala—Leu—Ala—Lys—CO—R

The cecropins are similar in structure to the bee venom toxin melittin, but have a broader antibacterial spectrum than mellitin, and do not lyse cultured liver cells, sheep erythrocytes or insect cells. As shown above, the carboxy terminus in all cecropins is blocked and, in the case of cecropin A, the blocking group is a primary amide (Andreu, et al., *Proceedings of the National Academy of Sciences*, USA, 80: 6475–6479 (1983)). Cecropin A and several related peptides have recently been synthesized by solid phase techniques and have been shown to be totally indistinguishable from natural cecropin A by chemical and physical criteria (Andreu, et al., supra).

Interestingly, the carboxy terminal tetrapeptide imide was found to be of little importance for the antibacterial activity towards *E. coli*, but for three other bacteria tested, the activity was reduced to 3% to 20% of that of cecropin A.

The cecropins are antibacterial against a variety of bacteria including both Gram-negative and Gram-positive bacteria. The available data on the mode of action of the cecropins indicate that they disrupt the cytoplasmic membranes of bacteria (Steiner, et al., *Nature*, 292: 246-248 (1981)). It is apparent from the literature that different bacterial species have different sensitivities to the cecropins, and that each cecropin has a distinct spectrum of activity. For example, *Bacillus megaterium* is highly sensitive to cecropins A and B, but relatively resistant to cecropin D. Both Gram-negative and Gram-positive organisms have been shown to be sensitive to cecropins in the micromolar concentration range. Organisms showing a high level of sensitivity to cecropins include *E. coli*, *Pseudomonas aeruginosa*, *Serratia marsescens*, *Xenorhabdus nematophilus*, *B. megatherium*, and *Micrococcus luteus*. Although cecropins A and B show a total of twelve amino acid replacements, their activities against nine different bacterial species are very similar, suggesting that many amino acid substitutions can be tolerated without altering the biological activity of the peptide. Similarly, cecropin B from the Chinese oak silk moth (*A. pernyi*) differs from cecropin B from North American silk moths (*H. cecropia*) at four positions; however, three of the changes are replacements for the corresponding amino acids found in the *H. cecropia* A form. The fourth change is in a position where *H. cecropia* A form. The fourth change is in a position were *H. cecropia* A and B therefore apparent that unique derivatives of the cecropins created by conservative amino acid substitutions would retain their biological activity. Non-conservative changes such as those found in cecropin D might be expected to alter the activity of the peptide. Cecropin D has almost as much activity against *E. coli* as cecropins A and B, but has significantly reduced activity against eight other species of bacteria.

In view of the great usefulness of the cecropins and analogues thereof and of the great promise that recombinant DNA methods offer for the production of proteins, it appeared desirable to provide a system for the production of cecropins by means of such technology.

SUMMARY OF THE INVENTION

It has now been found that the araB promoter can be used as a promoter in recombinant DNA molecules such that the araB promoter is operably linked to a heterologous gene that codes for a biologically active product. Using the araB promoter to control the expression of heterologous genes has many attendant advantages. The araB promoter control system is tightly regulated. The araB promoter is inducible with L-arabinose; e.g., produced polypeptides are not synthesized prior to addition of L-arabinose to the culture media. Thus, in the absence of L-arabinose there is no expression of the heterologous gene to form the polypeptides. Upon induction with L-arabinose, the polypeptide is transcribed as part of a messenger RNA which initiates at the araB promoter. Once induced, polypeptides are produced quickly and efficiently. Furthermore, the fermentation period is brief as compared with other systems. Importantly, the extent of expression is increased, i.e., the level of production of the heterologous polypeptide is greatly improved, thus making it desirable for commercial use. Finally, the expressed fusion polypeptides form inclusion bodies within the host cell that remain very stable, regardless of increased size, and are amenable to purification for heterologous protein.

According to the present invention there is thus provided a polynucleotide molecule expressible in a given host comprising the sequence of the araB promoter operably linked to a gene which is heterologous to said host. The heterologous gene codes for polypeptide(s) that is/are biologically active. The invention also provides for vehicles capable of replication and expression comprising said polynucleotide molecule; hosts transformed with said vehicle; and fermentation methods for cultivating said hosts for ultimate expression and recovery of the heterologous peptide(s).

The present invention also provides a process, and tools for use of the process, for the production of cecropin peptides and analogues thereof by recombinant DNA methodology. The cecropins can be expressed by using the aforementioned araB promoter or any other promoter.

In particular, the invention provides gene sequences coding for peptides having cecropin-like bactericidal activity. These gene sequences, which may be provided alone or as part of longer sequences comprising the cecropin peptide together with other peptides or amino acid residues, are, ideally, designed by computational methodology so as to optimize their acceptability by *E. coli* as expression hosts.

In particular, the invention provides a genetic construct capable of expression in a cecropin-sensitive host which is a fusion sequence between a first genetic sequence coding for cecropin operably linked to a second genetic sequence coding for a different polypeptide, wherein said different polypeptide is capable of suppressing the bactericidal effect of the expressed fusion product towards said cecropin-sensitive host.

In another embodiment, the invention provides a genetic construct capable of expression in a cecropin-sensitive host which comprises a genetic sequence coding for cecropin operably linked to an inducible promoter sequence.

The invention also provides vehicles capable of replication and expression comprising the aforementioned genetic constructs, hosts transformed with said vehicles, as well as methods of producing cecropins using the aforementioned vehicles, constructs and hosts.

The invention further provides a fusion protein of a cecropin with a polypeptide wherein said fusion protein has decreased bactericidal effects toward a given bacterial host.

Preferably, the genetic sequences coding for a cecropin are designed by computational methodology so as to optimize their acceptability by E. coli as expression hosts. Design optimization is also carried out to minimize self-complementarity, to avoid or create restriction endonuclease sites within or outside the sequence and thus facilitate insertion, and to minimize complementarity with the desired expression vehicles. By subjecting the polynucleotide sequence to such optimizations, the invention provides synthetic sequences which, in most instances, are structurally different from those in the natural genes of the various species used as sources for cecropin.

DESCRIPTION OF THE FIGURES

FIG. 7 shows the amino acid and nucleotide sequences of wild type and mutant cecropin A where
 (1) denotes CA wild type (pCA3D);
 (2) denotes CA mutant A (pCA3A); and
 (3) denotes CA mutant B (pCA3B);
denotes the position of mutation.

DEFINITIONS

Figure 1:
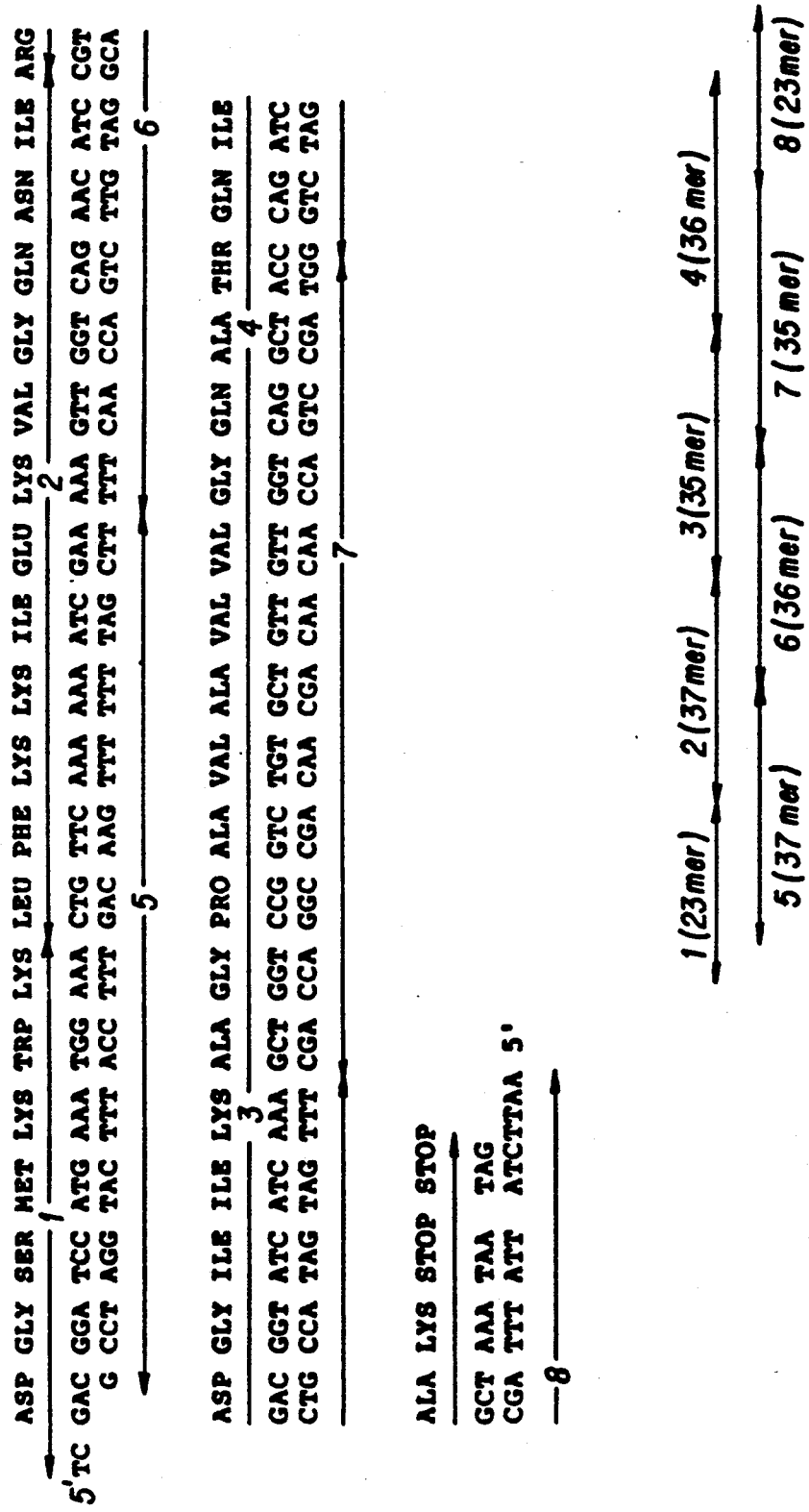
FIG. 1 shows the amino acid and nucleotide sequences of cecropin A and the synthetic gene used for expression in E. coli.

In the description that follows, a number of terms used in recombinant DNA technology are extensively utilized. In order to provide a clearer and consistent understanding of the specification and claims, including the scope to be given such terms, the following definitions are provided.

Operon—A gene comprising structural gene(s) for polypeptide expression and the control region which regulates that expression.

Operator—A DNA sequence capable of interacting with a specific repressor, thereby controlling the functioning of adjacent gene(s).

Promoter—A DNA sequence within the control region at which RNA polymerase binds and initiates transcription of an adjacent gene(s).

Activator—A protein required for initiation of RNA synthesis by RNA polymerase.

Initiator—A DNA sequence with which an activator interacts to control adjacent genes.

Polynucleotide molecule—A linear sequence of nucleotides linked together by a backbone consisting of an alternating series of sugar and phosphate residues and as used herein can include DNA and RNA polymers.

Structural gene—A DNA sequence which encodes through its template or messenger RNA a sequence of amino acids characteristic of a specific peptide.

Heterologous gene—A gene that is foreign, i.e. originating from a donor different from the host or a chemically synthesized gene and can include a donor of a different species from the host. The gene codes for polypeptides ordinarily not produced by the organism susceptible to transformation by the expression vehicle.

Biologically active—As used herein means the quality or process of accomplishing an intended effect occurring in a biological system.

Operably linked—As used herein means that the promoter controls the initiation of the expression the polypeptide encoded by the heterologous gene.

Expression—Expression is the process by which a structural gene produces a polypeptide. It involves transcription of the gene into messenger RNA (mRNA) and the translation of such mRNA into polypeptide(s).

Cloning vehicle—A plasmid or phage DNA or other DNA sequences which are able to replicate in a host cell, which are characterized by one or a small number of endonuclease recognition sites at which such DNA sequences may be cut in a determinable fashion without loss of an essential biological function of the DNA, and which contain a phenotypic selection marker suitable for use in the identification of transformed cells. Markers, for example, are tetracycline resistance or ampicillin resistance. The word "vector" is sometimes used for cloning vehicle.

Expression control sequence—A sequence of nucleotides that controls or regulates expression of structural genes when operably linked to those genes. They include the lac system, the trp system, major operator and promoter regions of phage lambda, the control region of fd coat protein, and other sequences known to control the expression of genes in prokaryotic or eukaryotic cells.

Expression vehicle—A vehicle similar to a cloning vehicle but which is capable of expressing a given structural gene in a host, normally under control of certain regulatory sequences.

Host—Any organism that is the recipient of a replicable expression vehicle, including bacteria and yeast.

Cecropin—This term as used throughout the specification and claims is meant to include a polypeptide from any insect species, which has bactericidal activity in an in vivo or in vitro system acceptable by the art to measure such activity.

The term cecropin is also used in this invention to include any analogue, homologue, mutant, isomer or derivative of a naturally-occurring cecropin, and which shows bactericidal activity in an appropriate system. The term is also meant to include fragments having less than the naturally-occurring number of amino acids, such as partial fragments of natural cecropins or their analogues. The term is also used to include any product which comprises the sequence of a naturally-occurring cecropin or analogue thereof, together with one or more flanking amino acids, preferably at the carboxy terminus, which show cecropin-like bactericidal activity. The term is also meant to include cecropins having less than the number of naturally-occurring amino acids but which still show bactericidal activity.

The degree of homology which brings a cecropin within the scope of this definition will vary depending upon the cecropin regions responsible for bactericidal activity; domains which are critical for bactericidal activity will exhibit a high degree of homology in order to fall within the definition, while sequences not involved in maintaining bactericidal conformation or in effecting receptor binding may show comparatively low homology. In addition, critical domains may exhibit bactericidal activity and yet remain homologous as defined herein if residues containing functionally similar side chains are substituted. "Functionally similar" refers to dominant characteristics of the side chains such as basic, neutral or acid, or the presence or absence of steric bulk. Generally, a peptide defined as a cecropin will contain regions substantially homologous with those of the cecropins shown in the section of this application entitled "Description of The Background Art."

Less homology is required in the amino terminal region than in the carboxy terminal region.

By "bactericidal activity" is meant to include activity as defined previously, which can either be greater or lesser than that of naturally-occurring cecropin species. In particular are included cecropin peptides having bactericidal activity which ranges from about 1% of the naturally-occurring species to activities which may be substantially higher (e.g., 10-fold, 100-fold, or higher) than those of the naturally-occurring cecropins.

BRIEF DESCRIPTION OF THE PREFERRED EMBODIMENTS

1. The araB Promoter

The present invention provides for a polynucleotide molecule expressible in a given host comprising the sequence of the araB promotor operably linked to a gene which is heterologous to said host. The heterologous gene encodes for polypeptide(s) that are biologically active. The invention also provides for associated constructs with the araB promoter. The araB promoter is an inducible promoter, i.e., the expression of the heterologous gene to form the encoded polypeptide is initiated or induced by the addition of L-arabinose. L-arabinose interacts with an activator, the product of the araC gene, to regulate expression of araB. This is a positive control system in contrast to a negative control system; for example, lac, trp, lamda $P_L$, and tac. Without the L-arabinose addition, the heterologous polypeptide will not be expressed or synthesized. Once induced, the biologically active polypeptide product(s) are produced quickly and efficiently. These polypeptide product(s) typically form as inclusion bodies within the host cells. The inclusion bodies enlarge rapidly as the cell density increases. The inclusion bodies remain very stable within the host cells. This characteristic results in a reproducible high yield and renders the fermentation monitoring an easy task. To terminate an on-going fermentation run, an accurate decision can be made simply based on the size of inclusion bodies and saturated growth.

The araB promoter and inferred amino acid sequence for the initial portion of the araC gene in *S. typhimurium* and plasmids pMH6 and pING1 has the following nucleotide sequence:

```
          +30         +20         +10         +1          -10         -20         -30
5'-CAATTGCCATCGTCTTACTCCATCCAGAAAAACAGGTATGGAGAAACAGTAGAGAGTCGCGGCAAAAACCGT

-40         -50         -60         -70         -80         -90         -100        -110
CAGGCAGGATCCGCTAATCTTATGGACAAAAATGCTAATGCTTTGCAAAGTGTGACGCTGTGCAAATATTCAATG

-120        -130        -140        -150        -160        -170        -180
TGGACATTTCCAGCCATAGTTATAGACACTTCTGTTACTTAATTTTATCGCCTGAACTGTACGCTTTTGTTACAAA

-190        -200        -210        -220        -230        -240        -250        -260
GCGCTTTTCACAAGCGGGGTTGATACGTGCTTTCATCAAGCGCAAAGTCTTGCGGAGACGGAAGCTCTGTCGTCC

-270        -280        -290        -300        -310        -320        -330
TGGTCGATATGGACAATTTGTTTCTTCTCTGAACATCGGGGGGTAGAGAAATC ATG GCT GAA ACG CAA ATT
                                                       Met Ala Glu Thr Gln Asn

-340        -350        -360        -370        -380
GAT CCG CTA TTG CCG GGA TAT TCA TTT AAT GCC CAT CTG GTC GCC GGG CTG ACG CCA
Asp Pro Leu Leu Pro Gly Tyr Ser Phe Asn Ala His Leu Val Ala Gly Leu Thr Pro
```

```
         -390        -400        -410        -420        -430        -440
                                         -continued
    ATT GAA GCG AAT GGA TAT CTG GAT TTT TTT ATC GAT CGT CCG TTG GGC ATG AAG GGA
    Ile Glu Ala Asn Gly Tyr Leu Asp Phe Phe Ile Asp Arg Pro Leu Gly Met Lys Gly -450        -460        -470        -480        -490        -500
    TAT ATT CTT AAC CTG ACC ATC CGC GGA GAG GGC GTC ATT AAT AAT AAT GGC GAG CAG
    Tyr Ile Leu Asn Leu Thr Ile Arg Gly Glu Gly Val Ile Asn Asn Asn Gly Glu Gln -510        -520        -530        -540        -550
    TTT GTC TGT CGG CCT GGC GAT ATA TTA TTG TTT CCG CCG GGC GAG ATT
    Phe Val Cys Arg Pro Gly Asp Ile Leu Leu Phe Pro Pro Gly Glu Ile
```

The araB promoter as part of the araB gene is located in the L-arabinose operon. The L-arabinose operon (araBAD) has been isolated in *E. coli* and *S. typhimurium*. However, the practice of this invention is not limited to these two sources for the araB promoter. Other sources can include any organism which contains genes coding for the L-arabinose operon. These sources for the araB promoter can include the genera Pseudomonas, Citrobacter, Xanthomonas, and Erwinia.

In addition, the araB promoter may be synthesized; e.g., by manipulation in the laboratory, rather than of natural origin. In other words, the concept connotes an artificially compounded or even an artificially degraded product. Thus, even though a given complete sequence for a naturally-occurring araB promoter may exist integrated into the genomic DNA of a given organism species, the isolated sequence corresponding to the araB promoter separated from the genomic DNA of the organism, with or without adjacent sequences corresponding to leading polypeptides, start or stop signals, is not naturally occurring and would be considered to be "synthetic." In addition, given the degeneracy of the genetic code, the knowledge of an amino acid sequence does not necessarily and irrevocably lead to the naturally occurring genetic sequence coding therefor.

Optimization of any synthetic sequence comprises four or more possible steps and is applicable to the synthesis of the araB promoter, as well as to synthesis of peptide sequences, including heterologous polypeptides. First, for any given desired sequence, a list of possible DNA codons for each amino acid in such sequence is generated, with those codons ranked in order according to the frequency with which they are used in bacteria or yeast. A preliminary ordering of the codons might be based on the paper by Bennetzen and Hall, *Journal of Biological Chemistry*, 257: 3026– 3031 (1982) (yeast) or Fiers, W., *Nature*, 260: 500 (1976) (bacteria), herein incorporated by reference. A further refinement of the sequence beyond the techniques of these papers is also recommended.

A second factor which influences the choice of any particular codon is the presence or absence of certain restriction enzyme sites that might be used in the process of clonging the gene, so that the use of those enzymes during the cloning process would be facilitated. Optimization of this factor comprises comparing the known endonuclease site sequences (comprising four to six nucleotides per site) with the primary "host-preferred" sequence. A list of restriction endonuclease sites can be found, for example, in Roberts, R. J., *Nucleic Acid Research*, 11: 1 (1983), r135–r137.

A third factor which influences the choice of particular codons is the need to minimize the internal secondary structure of the synthesized DNA fragments, to prevent them from folding upon themselves and inhibiting the annealing reactions to adjacent DNA fragments. This factor comprises searching a given design sequence so as to avoid undue complementarity of segments thereof, one with another, save for segments adjacent to one another in the intended gene. A search for complementarity (i.e., avoidance thereof) can also be carried out between the designed gene sequence and proposed replication vehicles, such as plasmids or phages.

A fourth factor involved in the optimization is the avoidance of sequences rich in AT base pairs (about 5 or more), especially when preceded by a sequence rich in GC base pairs, to avoid premature termination of transcription.

A fifth factor influencing the choice of codons is the avoidance of RNase sites so that the message is stable.

Finally, if any of two possible codons could be used, it is preferred to utilize that which will maximize expression in microbial genomes (see, for example, Fiers, et al., *Nature*, 260: 500 (1976); Grosjean, et al., *Gene*, 18: 199–209 (1982); and Riggs U.S. Pat. No. 4,366,246, column 6, all of which are herein incorporated by reference).

Most preferably, a computer program designed to carry out the necessary comparisons, to optimize expression in bacterial microbes or yeast, is utilized for the optimization.

In one embodiment of this invention, the inducible araB promoter is operably linked to a genetic sequence coding for a polypeptide that is biologically active, and the resulting genetic construct is introduced into or forms part of an expression vehicle. The expression vehicle is then utilized to transform an appropriate host. The host is fermented under selected culturing conditions to achieve optimum growth. The araB promoter is not active until treated with L-arabinose, which induces the promoter to initiate expression of the heterologous gene. The sequence of actions include transcription of the gene into mRNA, and the translation thereof into the polypeptide product(s).

In another embodiment of this invention, the araB promoter is operably linked to a genetic sequence coding for a heterologous polypeptide that is biologically active, and this genetic sequence is operably linked to a second genetic sequence coding for another polypeptide. The expression yields a fusion or precursor protein comprising both the amino acid sequence of the second polypeptide and that of the desired heterologous polypeptide, and containing a selective cleavage site adjacent to the desired amino acid sequence.

The cleavage site is preferably methionine, although the site may be any preferred site known in the art. The desired heterologous polypeptide should preferably lack internal cleavage sites corresponding to the actual selected cleavage site. Other known cleavage sites include Asn-Gly, Asp-Pro, Lys, Arg, and Lys-Arg.

Selective cleavage of the fusion or precursor protein is typically effected outside of the replicative environment of the expression vehicle. In this posttranslational step, the fusion or precursor protein is clipped by selective treatment. For example, when methionine is the cleavage site, the fusion or precursor protein is treated with cyanogen bromide to clip the desired heterologous polypeptide. With other known cleavage sites, the clipping treatment includes hydroxylamine, acid, trypsin, and Lys-Arg cleavage enzyme.

Methods for preparing fused, operably linked genes and expressing the same in bacteria are known and are shown, for example, in U.S. Pat. No. 4,366,246, herein incorporated by reference.

The genetic constructs and the methods involved herein can be utilized for expression of the heterologous polypeptides in bacterial hosts.

For example, E. coli K12 strain 294 (ATCC 31446) and strain MC1061 (ATCC 39450) are particularly useful. Other microbial strains which may be used include, but are not limited to, E. coli X1776 (ATCC 31537). The aforementioned strains, as well as E. coli W3110 (F−, lambda−, prototrophic (ATCC 27325)), and other enterobacteriaceae such as S. typhimurium or Serratia marcescens, and various pseudomonad species may be used.

In general, plasmid vectors containing replicon and control sequences which are derived from species compatible with the host cell are used in connection with these hosts. The vector ordinarily carries a replication site, as well as specific genes which are capable of providing phenotypic selection in transformed cells. For example, E. coli is typically transformed using pBR322, a plasmid derived from an E. coli species (Bolivar, et al., Gene, 2: 95 (1977)). pBR322 contains genes for ampicillin and tetracycline resistance and thus provides easy means for identifying transformed cells. The pBR322 plasmid, or other microbial plasmids must also contain, or be modified to contain, promoters which can be used by the microbial organism for expression of its own proteins.

The araB promoter may be operably linked to a genetic sequence coding for any heterologous polypeptide or protein that is biologically active. Examples of such polypeptides or proteins include, but are not limited to, enzymes, hormones, hemoglobin, antibodies, structural proteins, alpha, beta and gamma interferons, interleukins, insulin, and tissue plasminogen activators. Specific examples include human tumor growth factor, calcitonin, and cecropin.

The transformed host can be fermented and cultured according to means known in the art to achieve optimal cell growth. The preferred fermentation and production procedure of this invention, described below, can be used to achieve large scale production of heterologous polypeptides. In addition, by using the araB promoter operably linked to the heterologous gene, the extent of expression of the heterologous gene is increased.

The preferred fermentation procedure is as follows: The transformed host, preferably bacteria, more preferably E. coli, is introduced into a culture medium containing nutrient materials that meet the growth requirements of the bacterium. Such materials may include carbon and nitrogen sources, minerals, amino acids, purines, pyrimidines, and vitamins. The preferred culture medium also comprises a metabolite in an amount sufficient for phenotypic marker resistance, such metabolite being, for example, tetracycline or ampicillin. The host is grown under culturing conditions selected to achieve maximum growth rate. Temperature conditions will depend upon the host, but typically the optimum range is about 30° C. to about 40° C., with 37° C. being the most preferred for transformed E. coli. Oxygen is also provided to the medium. The host is allowed to grow until late exponential phase and then transferred to fresh culture medium.

The hosts are then inoculated with production culture medium. During this step, the bacteria will continue to divide and grow until the bacteria reach a concentration, saturation density, at which the bacteria no longer divide, but are still viable. The time sufficient to reach the saturation density is dependent on the medium, the genotype of the host, the temperature, and the degree of aeration.

Initially, the fermentation and culturing conditions for the production step are the same as those given above for the culture step, except that as dissolved oxygen is consumed during growth, the agitation and aeration rate are increased accordingly to maintain a minimum dissolved oxygen (D.O.) at 30%. The preferred pH range is between about 6 to 8. The pH of the above-described production medium is consistently self-adjusted at 6.5–6.8, which is optimum for E. coli growth. Thus, acid and base control of the pH medium is unnecessary for the E. coli host; however, it may be necessary to adjust the pH medium for other hosts. When optimal cell density is reached, optimally $OD_{600}10$ for E. coli, L-arabinose is added in an amount sufficient to induce the synthesis of the heterologous gene to form the polypeptide. As described above, the polypeptide forms inclusion bodies within the host. The peptide is then recovered according to means known in the art such as filtering or precipitation. If a fusion protein is the resulting expressed heterologous peptide, the fusion protein is recovered and then may be treated in a post-translation step to separate the desired heterologous polypeptide. The heterologous polypeptide can then be recovered and purified according to known means.

The use of the araB promoter will be described, for convenience, relating to various embodiments of the invention comprising cecropin, although it is to be understood that the araB promoter may be operably linked to a genetic sequence coding for any polypeptide or protein that is biologically active.

2. Methods of Microbial Production of Cecropins Using Cecropin-Sensitive Hosts

Part of the present invention also provides methods of microbiological production of cecropins using cecropin-sensitive hosts. One concept of the invention is to express a gene sequence coding for cecropin while, simultaneously, avoiding or delaying the bactericidal effects of the product.

In a one embodiment, the genetic sequence coding for cecropin is linked to an inducible promoter, and the resulting genetic construct is introduced into an expression vehicle. The expression vehicle is then utilized to transform an appropriate host and the host is fermented under normal conditions wherein the promoter is not active. After an appropriate period of time, such as, for example, at a time when the cells are in stationary phase, the promoter is induced as by varying an outside environmental factor such as salt concentration, light, presence or absence of a metabolite, a metal, and the like, this change leading to transcription of the cecropin genetic sequence into mRNA, and then translation thereof into bactericidal cecropin. Even though the resulting cecropin is bactericidal and destroys the bacterial host, such destruction does not occur until late in the fermentation cycle. Examples of regulated promoters are lambda $P_L$ and $P_R$, lac, gal, trp, ara, hut, and the like.

In the second preferred embodiment, it has been discovered that if a genetic sequence coding for cecropin is operably linked to a polypeptide other than said cecropin, such that the expression yields a fusion or precursor protein comprising both the amino acid sequence of cecropin and that of the additional polypeptide, and containing a selective cleavage site adjacent to the desired cecropin amino acid sequence, the resulting fusion protein is not bactericidal. Bactericidally active cecropin can then be isolated post-translation by selective cleavage.

Most commonly, cleavage will be effected outside the replicative environment of the expression vehicle, such as, for example, following harvest of the microbial culture. Thus, the additional polypeptide robs the cecropin of its bactericidal effect pending extracellular cleavage, allowing the survival of the host for long enough time to yield high levels of the desired product. Preferably, the cecropin will lack internal cleavage sites corresponding to the selective cleavage site employed to shed the superfluous polypeptide, although this is not necessarily an absolute condition. Since the cecropins are methionine free, cyanogen bromide cleavage at the methionine adjacent to the cecropin sequence is effective.

Preferably, the genetic sequence coding for the superfluous polypeptide is transcribed in advance of the structural gene of the cecropin, but this need not necessarily be the case, as it may also be possible to express the superfluous polypeptide in a position adjacent to the C-terminal of the cecropin.

The nature of the superfluous adjacent polypeptide is not critical. It could either be part, whole or repetitive units of a known structural, enzymatic, hormonal, or other physiologically relevant proteins. Alternatively, it could be a non-functional polypeptide. Without being bound by any particular theory, the inventors speculate that the increased length of the fusion protein somehow "masks" the bactericidal properties of the cecropin due to the varying conformation of the overall polypeptide. Preferably, the genetic sequence coding for the adjacent superfluous polypeptide should be at least about greater than 300 base pairs in length, preferably between about 400 bp and 5 Kb, most preferably between 400 bp and 2 Kb. This corresponds to a superfluous polypeptide of preferably between about 100–1700 amino acid residues.

Any of a large number of superfluous polypeptides can be fused to the desired cecropin peptide sequence. The polypeptide gene sequence can either be prepared by organic synthesis, in which case optimization procedures would be recommended, or might be prepared by such techniques as reverse transcription of appropriate mRNA. Enzymatic coupling of the gene sequence for the polypeptide to the gene sequence for the structural cecropin peptide would then follow the preparation of the cDNA. Enzymatic coupling can be either by blunt ligation or by the provision of cohesive termini, comprising one of the two strands of a restriction endonuclease recognition site. Examples of superfluous polypeptides are beta-galactosidase or ribulokinase (encoded for by the araB gene). Enzymes and structural proteins are preferred. Other products which can be used are products encoded by the following genes: aceA or aceB, araA, araB, araC, araD, argG, aroB, lacA, serA, purA, trpA, trpB, trpC, trpD, trpE, tyrA, and the like. The superfluous polypeptide is normally free of glycosylation. The araB promoter is the preferred promoter, although other promoters such as lambda $P_L$ and $P_R$, lac, gal, trp, hut, and other ara promoters may be used.

In yet another embodiment of the invention, the cecropin genetic sequence is operably linked to the sequence for a superfluous polypeptide capable, in the fusion product, of inhibiting or inactivating the bactericidal activity of cecropin and, in addition, to an inducible promoter. In this manner, both the effect obtainable through the fusion protein technique and the effect obtainable through the use of the inducible promoter can be exploited advantageously and simultaneously.

Although the present invention results in methods for producing cecropins in cecropin-sensitive hosts, e.g., bacterial hosts, the genetic constructs prepared herein and the methods involved can also be utilized for expression of cecropin in other, non-cecropin sensitive hosts. These non-cecropin sensitive hosts include yeasts and mammalian cell cultures. Useful yeast and mammalian hosts and vectors are well known to those of skill in the art, and reference is made, for example, to European Patent Publication 0093619 published Nov. 9, 1983. Bacterial hosts can include those mentioned hereinabove with the araB promoter, as well as bacterial hosts such as the genera Pseudomonas, Citrobacter, Xanthomonas, and Erwinia. Any plasmid vector compatible with these hosts, as described above with the araB promoter, can be used.

Another preferred promoter for cecropin is lambda $(P_L)$. The genetic construct for cecropin and the superfluous polypeptide can be placed under the control of the leftward promoter of bacteriophage lambda $(P_L)$. This promoter is one of the strongest known promoters which can be controlled. Control is exerted by the lambda repressor, and adjacent restriction sites are known. A temperature sensitive allele of CI gene can be placed on the vector that contains the cecropin complete sequence or a different vector. When the temperature is raised to 42° C., the repressor is inactivated, and the promoter will be expressed at its maximum level. The amount of mRNA produced under these conditions should be sufficient to result in a cell which contains about 10% of its newly synthesized RNA originated from the $P_L$ promoter. In this scheme, it is possible to establish a bank of clones in which a functional cecropin fusion construct sequence is placed adjacent to a ribosome binding sequence, and at varying distances from the lambda $P_L$ promoter. These clones can then be screened and the one giving the highest yield selected.

The expression of a cecropin sequence can also be placed under control of other regulons which may be "homologous" to the organism in its untransformed state. For example, E. coli chromosomal DNA contains a lactose or lac operon which mediates lactose digestion by elaborating the enzyme beta-galactosidase. The lac control elements may be obtained from bacteriophage lambda plac5, which is infective for E. coli. The phage's lac operon can be derived by transduction from the same bacterial species. Regulons suitable for use in the process of the invention can be derived from plasmid DNA native to the organism. The lac promoter-operator system can be induced by IPTG.

Of particular interest in the present invention is to provide synthetic polynucleotide sequences coding for the cecropin peptides. In a preferred embodiment of the present invention, the synthetic sequence of the cecropin peptide (with or without adjacent sequences) is optimized so that expression thereof will be compatible with a variety of hosts such as yeasts and bacteria, especially the latter. In particular, optimization of the expression of any given sequence in $E.\ coli$ is of great importance. Thus, after performing such optimization procedures as indicated above, the actual genetic sequence of the cecropin peptides with or without adjacent sequences, will usually be distinct from the naturally-occurring sequence in the original species.

In addition, the design of the desired gene for the fused product should preferably incorporate codons for amino acids at the cleavage site as methionine (cleavable by cyanogen bromide), tryptophan (cleavable by o-iodosobenzoic acid), glutamic acid (cleavable by Staph. protease) and the like.

In one embodiment of the invention, any given codon in the desired DNA sequence for the fusion product can be mutagenized at will through sitedirected mutagenesis. Thus, it is possible, after synthesis of the desired DNA sequence, to introduce into the sequence a cleavable site. Site-directed mutagenesis is known, and reference is made to Wallace et al., *Science*, 209: 1396–1400 (1980), herein incorporated by reference.

The amino acid residue or residues following the potential C-terminal residue in the cecropin-peptide may be followed by yet another polypeptide ("trailing" polypeptide) of varying length and of structure similar or different than a leading polypeptide if one is present, as described above. In such case, it is convenient to provide for the same or different selective cleavage sites between the C-terminal amino acid residue and the trailing polypeptide sequence. These cleavable sites may or may not be the same as those present between the leading polypeptide and the structural gene for the cecropin peptide.

In other words, the superfluous polypeptide may be present as a leading peptide, a trailing polypeptide or both.

Where the structural gene of the desired cecropin peptide is to be inserted into a vehicle for expression as such, the gene would be preceded by a "start" codon, and if followed by trailing sequences, one or more termination or stop codons. When the expression product is a fusion protein comprising both the cecropin peptide and part or whole of a polypeptide, the start codon may be placed prior to the N-terminus of the polypeptide if it is leading.

Methods for the syntheses of polynucleotides are well known to one skilled in the art. Reference is made, for example, to the triester method of Itakura et al., *Journal of American Chemical Society*, 97: 3727 (1975).

The cecropins produced by the methods of the invention can be used as broad anti-microbial agents directed toward specific applications. Such applications include, for example, the use of the cecropins as preservatives in processed meat products (target organisms: (1) *Clostridium botulinum*, (2) Lactobacilli, (3) Micrococci); anti-caries agents in oral hygiene products (target organism: Streptococcus mutans); agents useful in the treatment of vaginal yeast infections (target organism: *Candida albicans*); and as anti-bacterial agents in deodorants (target organisms: (1) Micrococci, (2) Diphtheroids). The relative effectiveness of cecropin-like peptides for the applications described can be readily evaluated by one of skill in the art by determining sensitivity of any organism to one of the cecropin peptides. The same bacterial screen used in vitro can be utilized to determine dosages and concentrations.

Having now generally described this invention, the same will be better understood by reference to a specific example which is included herein for purposes of illustration only and is not intended to be limiting unless otherwise specified.

METHODS

Amino Acid Compositions

Hydrolysis of cecropin polypeptides was accomplished using 5.5M HCl (Pierce) at 110° C. for 24 hours in vacuo. Samples were dried under vacuum at 40° C. and resuspended in 200 ul of Beckman Model 6300 sample buffer (low pH citrate).

Amino acid analysis was performed using a Beckman Model 6300 analyser. Postcolumn ninhydrin was used for detection. Data was recorded using a Hewlet Packard (HP) integrator Model 3390. The individual peaks were recorded as the sum of the signals at 540 and 440 nm. Beckman standards containing each amino acid were used to calibrate the integrator and sperm whale myoglobin (Applied Biosystems) was used to verify the calibration.

Protein Sequencing

An Applied Biosystems Model 470A protein sequenator was used for all protein sequence determinations. Specifications for the sequencing methodology follow the Hunkapiller-Hood program. The system uses a non-vacuum program with cleavage by methanolic-HCl.

PTH Determinations

PTH determinations were accomplished using an HP model 1090A HPLC with an HP model 3390A integrator for data presentation. An IBM cyano-propyl column was used for separation of the PTH amino-acids. The buffer was 30 mM NaHAc pH 5.1 containing 5% tetrahydrofuran. The flow rate was 1 ml./min. and temp. 37° C.

Samples were dissolved after drying in vacuo with 30 ul of 33% acetonitrile in water for 30 min. The PTH standards used were from Pierce Chemical Co.

EXAMPLE 1

Synthesis and Cloning of a Synthetic Cecropin A (CA) Gene

A. Synthesis of the CA Gene

A gene coding for CA was designed by computer to incorporate codons normally found in highly expressed $E.\ coli$ proteins. At the end of the gene were incorporated 4-bp overhangs to permit the ligation of SalI and EcoRI sites respectively. To facilitate the construction of various sizes of fused proteins a BamHI site was included following the SalI site. Also, by using a computer program, optimization procedures as described previously were taken into account. The gene was divided into eight oligonucleotides ranging from 23 to 37 bases in length (FIG. 1).

The eight single-stranded DNA fragments were synthesized according to the solid-phase phosphotriester method as described by Ito, et al., *Nucleic Acids Research*, 8:5491 (1982).

Several modifications and improvements were made, including the following:

(1) The coupling reaction was carried out at 37° C. for 40 minutes with gentle shaking.

(2) For the deprotection of the DNA after final coupling reaction, the DNA resin (10 mg) was reacted with a 0.5M 2-pyridinealdoxime-tetramethyl guanidinium solution (2 ml) in pyridine-water (8:2 v/v) for 60 hours at 37° C. with shaking. The combined solution was evaporated and treated with NH$_4$OH (28%, 3 ml) in a sealed ampoule at 60° C. for 36 hours. After evaporation of the ammonia, the solution was extracted with ether three times and then evaporated. For the purification of the DNA, the residue was dissolved in 0.1 ml of 50 mM triethylammonium bicarbonate pH 7.5 (TEAB) and applied to a Sephadex G-50 column (1×50 cm). One ml fractions were collected. The first few fractions, at the leading edge of the major 260 nm-absorbing peak, contained the desired product. These fractions were evaporated, then purified further by high pressure liquid chromatography (HPLC). HPLC purification was carried out on a Bondapak C18$^R$ (Waters) column at 55° C. using a linear gradient of acetonitrile (10–40%) in 10 mM triethylammonium acetate buffer (pH 7.8). The DMT group was hydrolyzed by treatment with 80% acetic acid (0.1 ml) for 25 minutes at room temperature followed by evaporation and then evaporated with 0.1 ml water to remove the acetic acid completely.

B. CA Gene Assembly by Ligation

The 5'OH termini of the chemically synthesized fragments 1 through 8 were separately phosphorylated in the presence of 10 ul of solution containing:
70 mM Tris-HCl (pH 7.6)
10 mM MgCl$_2$
5 mM dithiothreitol
66 uM gamma-$^{32}$P-ATP (1 uCi)
400 ng of DNA and 2 units of T4 polynucleotide kinase.

The reaction was held at 25° C. for 15 minutes then 1 ml of 10 mM unlabelled ATP was added to continue the reaction for another 15 minutes. To check the purity, 10% of the phosphorylated DNA was analyzed by the standard method using polyacrylamide gel (15%) electrophoresis in the presence of 7M urea.

Four hundred ng of the phosphorylated DNA fragments 2, 3, 4, 5, 6 and 7 were heated at 95° C. for five minutes to inactivate the T4 polynucleotide kinase. Then 400 ng of unphosphorylated fragments 1 and 8 were added and heated at 95° C. for another five minutes and then cooled to 25° C. slowly (1° C. per 10 min.). The eight DNA fragments were ligated in a total volume of 100 ul in the presence of 66 mM Tris-HCl (pH 7.5), 6.6 mM MgCl$_2$, 10 mM dithiothreitol, 0.4 mM ATP and 2 units of T4 DNA ligase for two hours at 25° C.

C. Construction of Plasmids pING 1, pCA1A, pCA1B and pCA1'

Figure 2:
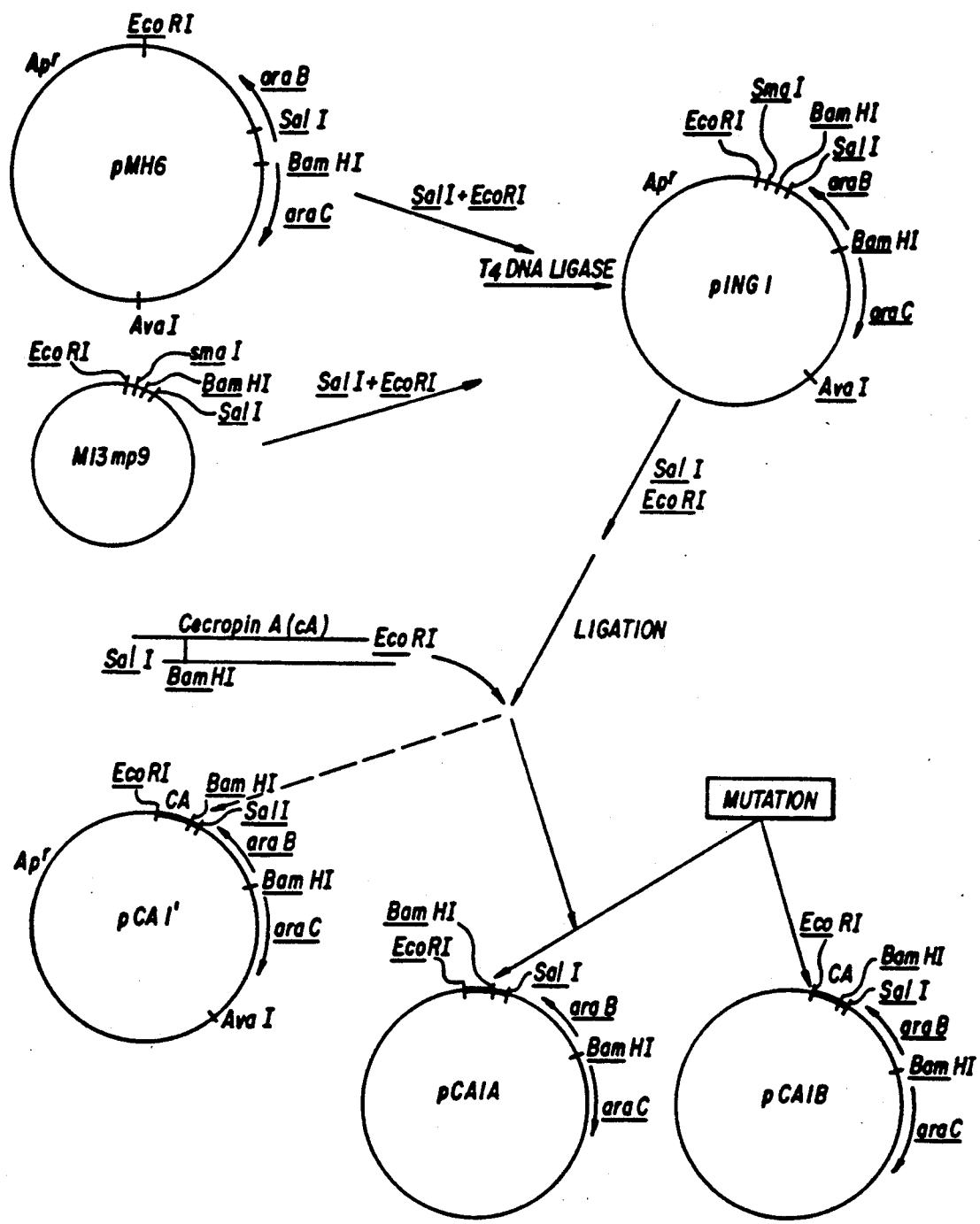
FIG. 2 shows the construction of plasmid pING 1 from plasmid pMH6 and M13mp9. pING 1 carries both the Salmonella typhomurium araB and araC genes from plasmid pMH6. The Figure also shows the construction of plasmids pCA1A, pCA1B and pCA1' from plasmid pING1 (as the source of the araB and araC genes).

The construction scheme is shown in FIG. 2. The sequence of the araB promoter is described in Horwitz, A. H. et al., *Gene*, 14:309–319 (1981). pMH6 is described in line, H.-C. et al., *Gene* 34:111–122 (1985) and M13mp9 is commercially available.

1. The CA gene fragments obtained from Step B, supra, were ligated to plasmid pING 1 which had been pretreated with restriction endonuclease SalI and EcoRI, then digested with restriction endonuclease SmaI to decrease the transformants carrying pING 1.

2. The SmaI-treated plasmid was transformed into *E. coli* MC1061.

Figure 7:
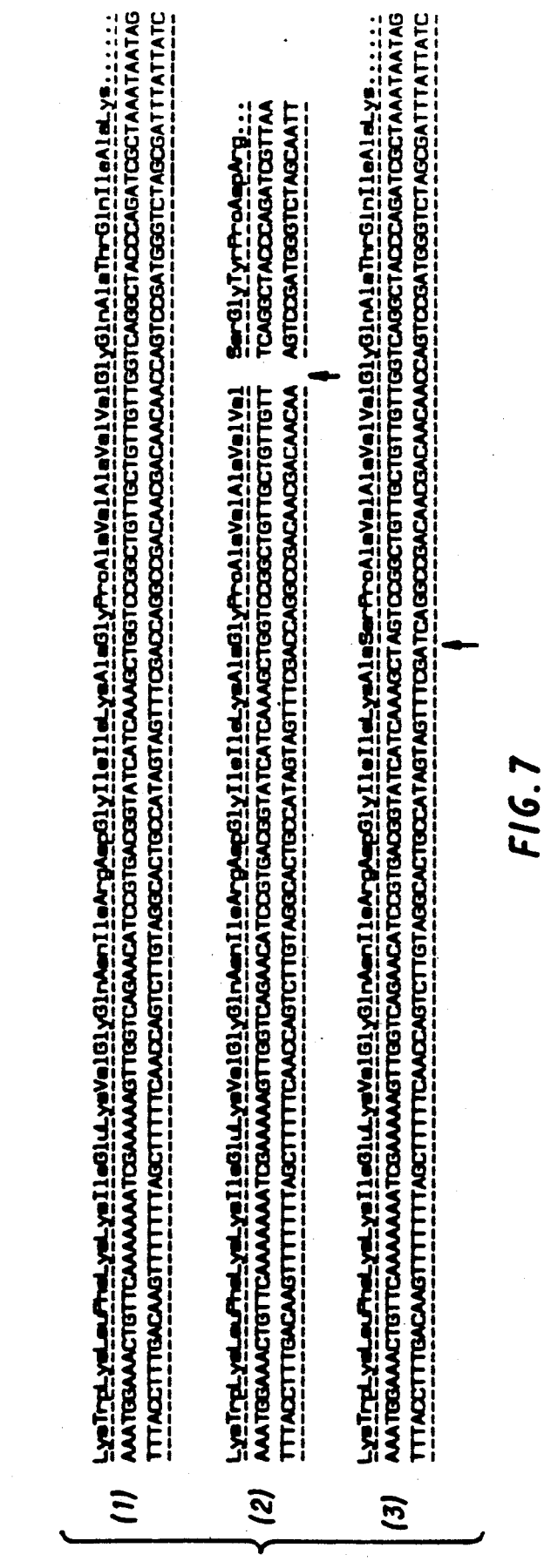

3. The colonies which contained plasmids carrying the CA gene fragment were identified by colony hybridization using the synthetic DNA fragment 7 (FIG. 1) as a probe. Three independent clones which contained the CA fragment were found in 1,000 colonies. Each of the isolated plasmids was digested with SalI and EcoRI to check the size of the excised fragment. The nucleotide sequence analysis of the CA insert was performed by the dideoxy chain termination procedure of Sanger et al., *PNAS*, 74: 5463–5467 (1977) with some modification (Wallace et al., *Gene*, 16:21–26 (1981)). Two sequences were determined and are shown in FIG. 7(2) and 7(3). The plasmids containing these sequences were designated pCA1A and pCA1B (FIG. 2). Each of these sequences differed from the wild type CA sequence at the positions indicated by the arrows in FIG. 7(2) and 7(3).

Various methods can be used to generate a wild-type sequence, for example in vivo or in vitro recombination of pCA1A and pCA1B or screening of additional independent clones. The plasmid containing the proposed wild type sequence is designated pCA1' (FIG. 2).

In the description that follows, plasmids with primes (') denote wild type CA sequences, whereas plasmids without primes are derived from mutants pCA1A or pCA1B.

D. Construction of plasmids pCA2', pCA2A pCA3', pCA3A and pCA3B

Figure 3:
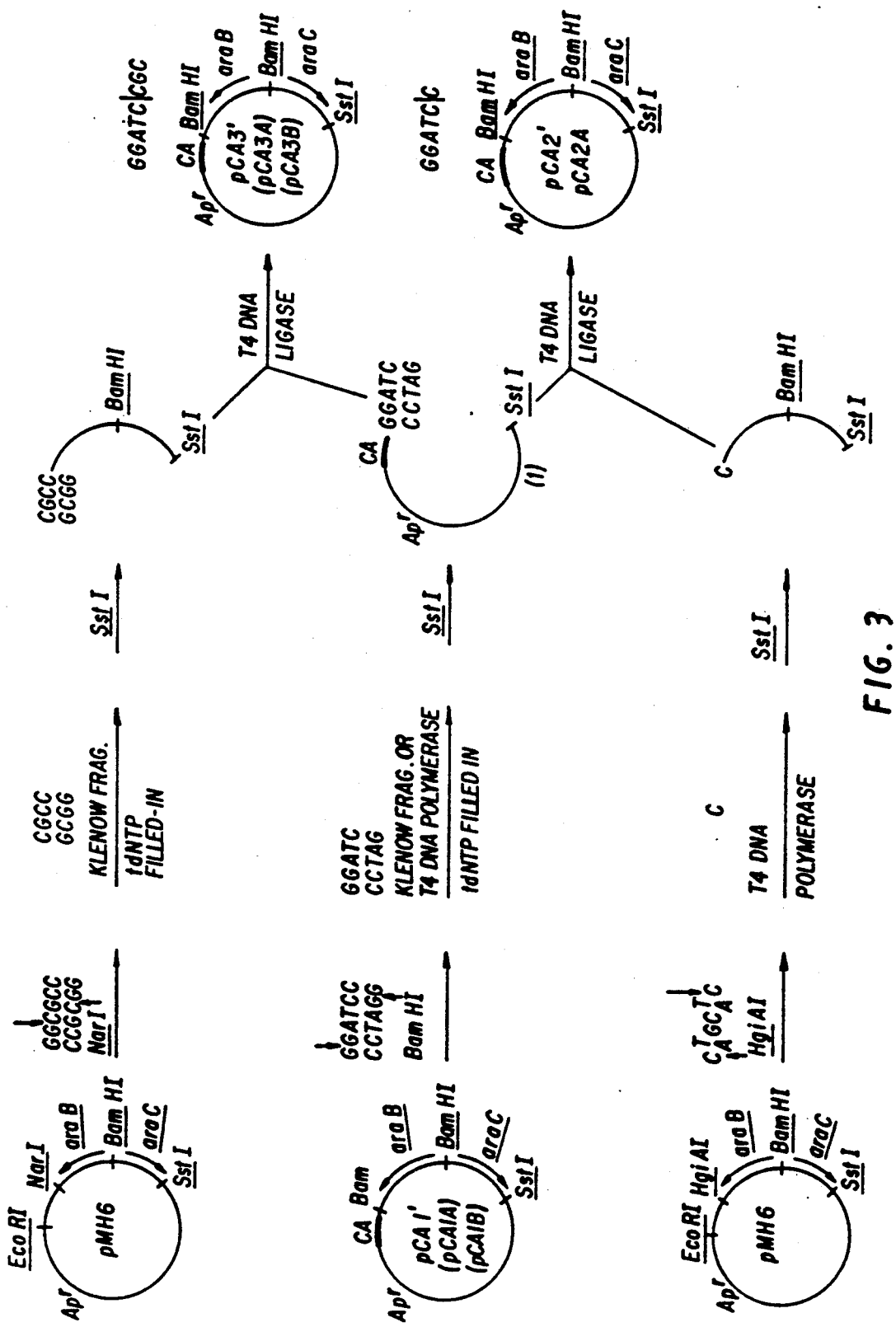
FIG. 3 shows the construction of plasmids pCA3', PCA3A, PCA3B and PCA2' and PCA2A from pMH6 and pCA1A, pCA1B and pCA1'. The differences between pCA1' (or pCA1A and 1B), pCA2' (or pCA2A) and pCA3' (or pCA3A and pCA3B) lie in the varying length between the cecropin A gene and the BamHI site between both ara genes, being 500 bp in pCA1' (or pCA1A and 1B), 1253 bp in pCA2' (or pCA2A) and 1550 bp in pCA3' (or pCA3A and 3B).

This is shown in FIG. 3. pCA1' (or pCA1A or pCA1B) is digested with BamHI and, after treatment with polymerase plus dTNP, followed by SstI digestion, yields a fragment (1) which is blunt ended at one end and carries an SstI overhang at the other. This fragment is ligated with a fragment obtained from pMH6 by NarI digestion, blunt end formation and SstI treatment, to give, after T4 ligation, pCA3' (or pCA3 or pCA3B). The fragment (1) is also ligated with a fragment obtained from pMH6 by HgiAI digestion, blunt end formation and SstI treatment, to give, after T4 ligation, pCA2' (or pCA2A).

The desired products are sought by transforming *E. coli* MC1061 with the ligation products. Plasmids are isolated by the minilysate procedure indicated supra. Each of the isolated plasmids is digested with BamHI and PstI respectively. Plasmids from each group having the correct size and correct orientation of the BamHI fragment are designated pCA2' (or pCA2A) and pCA3' (or pCA3A or pCA3B).

E. Expression of araB-CA fusion protein

*E. coli* cells containing araB-CA fused genes in plasmids pCA1A, pCA2A, pCA3A, pCA3B and pCA3D (note: pCA3D will hereafter interchangeably be used to denote wild type CA containing plasmid pCA3') were grown at 37° C. in media containing 1.5% tryptone, 1.0% yeast extract and 0.5% NaCl (TYE) with ampicillin at 50 ug/ml. At cell densities of OD$_{600}$=0.2, cultures were treated with L-arabinose to a final concentration of 0.5% to induce expression of araB-CA fusion protein, and were harvested when cell densities reached OD$_{600}$=1.5 to 1.7, by centrifugation at 4000 RPM at 4° C. for 20 minutes in a Beckman JS-4.2 rotor. Cells were washed once by resuspending in one-half original culture volume of 50 mM phosphate buffer (pH 6.6).

Washed pellets of cells containing plasmids pCA1A, pCA2A, and pCA3A were extracted in one-tenth volume phosphate buffer and 1% sodium dodecyl sulfate (SDS) and analyzed on a 10% polyacrylamide SDS-denaturing gel. By this analysis, it was shown that *E. coli* cultures containing plasmid pCA3A produced more araB-CA protein than either pCA1A or pCA2A-transformed culture.

F. Fractionation of induced *E. coli* cells containing plasmids pCA3A, pCA3B and pCA3D Washed pellets from Step E were resuspended in one-tenth original volume of phosphate buffer, chilled to 0° C., then the cell was broken in a French pressure cell. The subcellular components were then centrifuged at 4000 RPM at 4° C. for 20 minutes in the rotor. Analysis of the resulting supernatant and 4000 RPM pellet on a 10% polyacrylamide SDS denaturing gel showed that all of the araB-CA fusion protein of pCA3A, 3B and 3D were found in the 4K pellet.

G. Purification of the synthetic CA (a) Cyanogen bromide cleavage

1. The 4K pellet fraction which contained the araB-CA fused protein obtained from the last step was mixed with 90% formic acid to give 0.7–1.1 mg/ml protein in 70% formic acid. A 10-fold excess of cyanogen bromide (1 gm/ml stock in acetonitrile) by weight was added. The reaction mixture was flushed with nitrogen and incubated at room temperature overnight.

2. The formic acid and cyanogen bromide were removed under a stream of nitrogen. The residue was dissolved in 70% formic acid and dried under a stream of nitrogen twice more.

3. A solution of 0.1% trifluoroacetic acid in water was added; this dissolved the cleaved CA completely at 1 mg protein/ml.

(b) High pressure liquid chromatography of cyanogen bromide fragments

The cyanogen bromide-cleaved fused protein was chromatographed by HPLC to isolate the fragment from the CA portion of the molecule. A C-18 reverse-phase column (Waters) was used. A gradient was run with 0.1% trifluoroacetic acid (TFA) in water (buffer A) and 0.1% TFA in acetonitrile (buffer B). The starting eluent contained 20% buffer B; at 2 minutes after sample injection, a gradient of 20% B to 60% B over 60 minutes was initiated. The flow rate was 1 ml/minute. The elution profile was monitored at 280 nm. Various peaks in the chromatogram of the cyanogen bromide-cleaved fused protein which eluted were collected to test the bactericidal activity as described later below (Example 4).

H. pCA3A Codes for a Mutant Cecropin Polypeptide

TABLE I

Amino Acid Composition of Cecropin-A Produced by pCA3A in E. coli

| Amino Acid | Mutant A | |
|---|---|---|
| | Experimental Values | Theoretical Values* |
| Asp | 2.9 | 3 |
| Thr | 0.1 | 0 |
| Glu | 2.7 | 2 |
| Pro | 2.4 | 2 |
| Gly | 6.3 | 4 |
| Ala | 3.0 | 3 |
| Val | 3.6 | 4 |
| Ile | 2.9 | 4 |
| Leu | 1.2 | 1 |
| Phe | 1.1 | 1 |

TABLE I-continued

Amino Acid Composition of Cecropin-A Produced by pCA3A in E. coli

| Amino Acid | Mutant A | |
|---|---|---|
| | Experimental Values | Theoretical Values* |
| Lys | 6.2 | 6 |
| Arg | 2.1 | 2 |
| Trp | ND | 1 |
| Ser | 1.3 | 1 |
| Cys | 0 | 0 |
| Met | 0 | 0 |
| Tyr | 0.1 | 0 |
| His | 0.4 | 0 |

N.D. = not determined.
*Theoretical Values: Obtained from DNA sequencing analysis of each mutant clone.

The nucleic acid and the amino acid sequences are shown in FIG. 7.

EXAMPLE 2

Demonstration of Another Mutant Cecropin Polypeptide

The cells of plasmid pCA3B were fractionated, CA sequences were detected, and the synthetic CA was purified and analyzed as shown in Example 1, Parts F–G. Amino acid composition and sequence data, shown in Table II, indicated that the second clone also contained a CA gene sequence coding for a mutant cecropin.

TABLE II

Amino Acid Composition of Cecropin-A Produced by pCA3B in E. coli

| Amino Acid | Mutant B | |
|---|---|---|
| | Experimental Values | Theoretical Values* |
| Asp | 2.3 | 2 |
| Thr | 1.0 | 1 |
| Glu | 4.2 | 4 |
| Pro | 1.0 | 1 |
| Gly | 4.1 | 3 |
| Ala | 5.0 | 5 |
| Val | 3.6 | 4 |
| Ile | 3.9 | 5 |
| Leu | 1.1 | 1 |
| Phe | 0.9 | 1 |
| Lys | 6.6 | 7 |
| Arg | 1.0 | 1 |
| Trp | ND | 1 |
| Ser | 1.1 | 1 |
| Cys | 0 | 0 |
| Met | 0 | 0 |
| Tyr | 0 | 0 |
| His | 0.1 | 0 |

N.D. = not determined.
*Theoretical Values: Obtained from DNA sequencing analysis of each mutant clones.

The nucleic acid and amino acid sequences are shown in FIG. 7.

EXAMPLE 3

Construction of Plasmid pCA3D Coding for Wild Type Cecropin A

Figure 4:
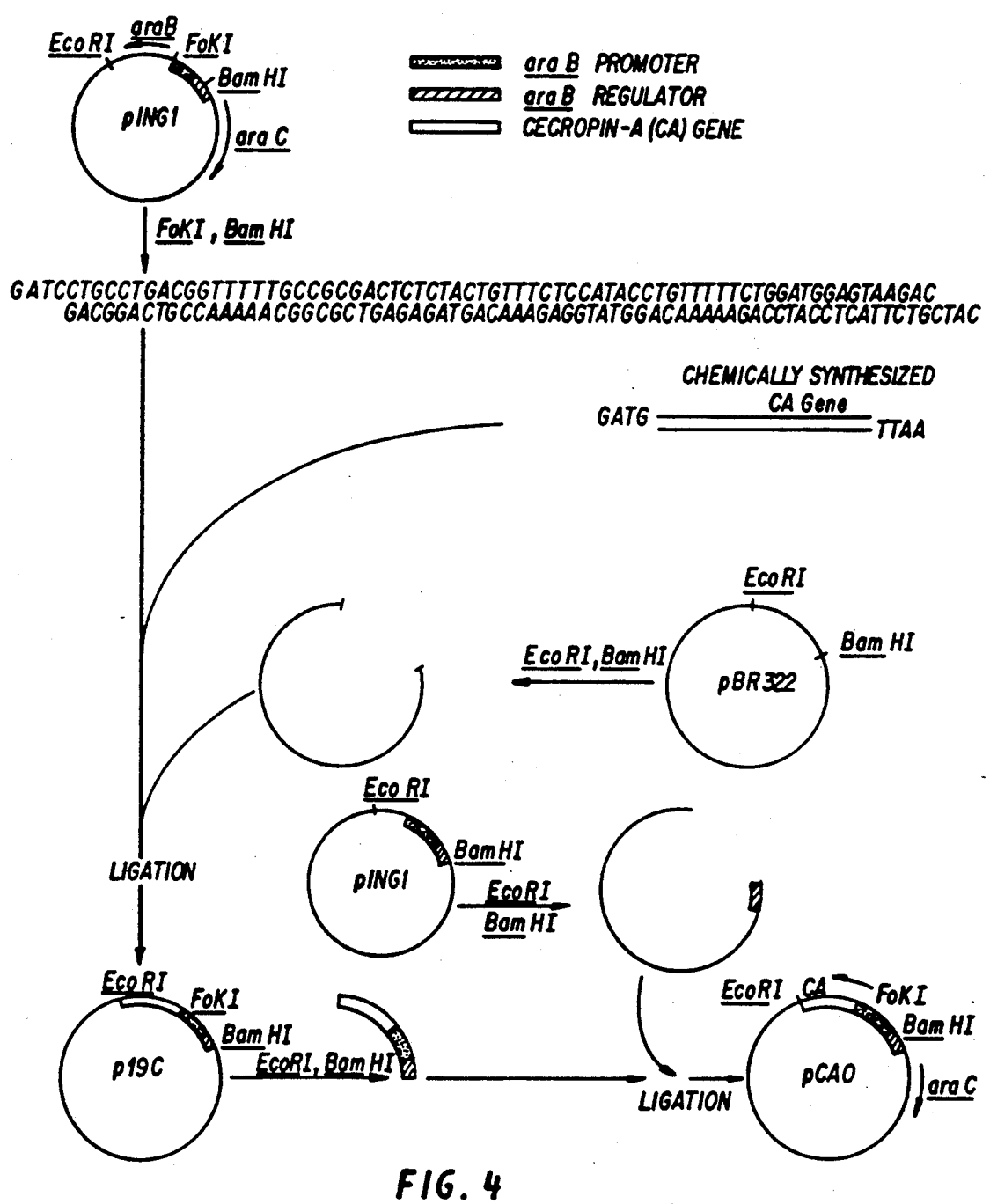
FIG. 4 shows the construction of plasmid p19C.
Figure 5:
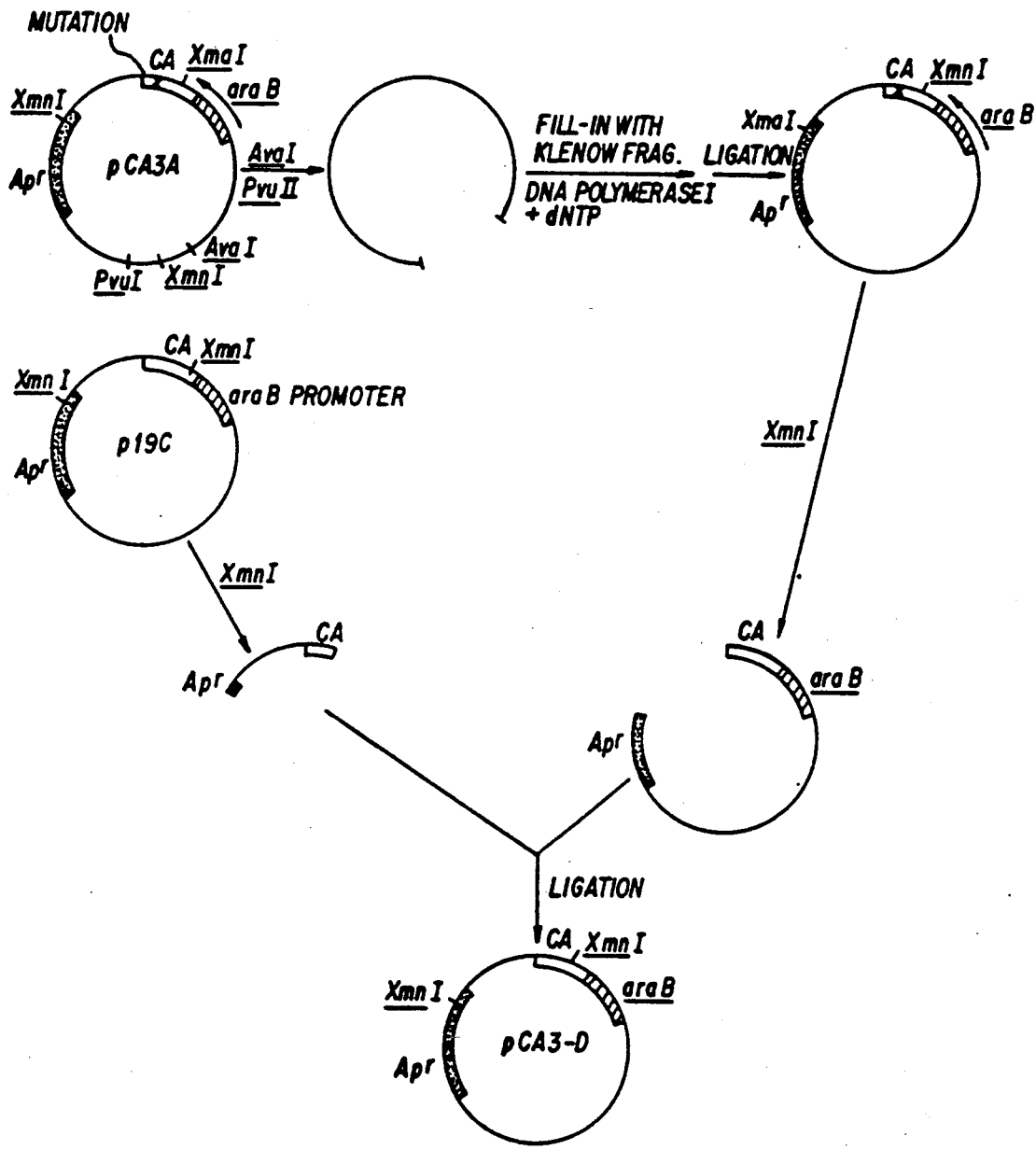
FIG. 5 shows the construction of plasmid pCA3A--1 from pCA3A. The Figure also shows the construction of plasmid pCA3D from pCA3A--1 and p19C (FIG. 4).

The construction scheme is shown in FIGS. 4 and 5.

A. Construction of pl9C

1. Plasmid pING 1 was digested to completion with endonucleases FokI and then BamHI; the resulting digestion was halted by phenol/chloroform (ratio 1:1) extraction and the aqueous residue was washed with ether and then passed through a Bio-Gel® P-10 column to remove the phenol/chloroform.

The result of FokI digestion produced a "CTAC" 5' overhang. This 76 base pair BamHI, FokI fragment contains the araB promoter.

Figure 6:
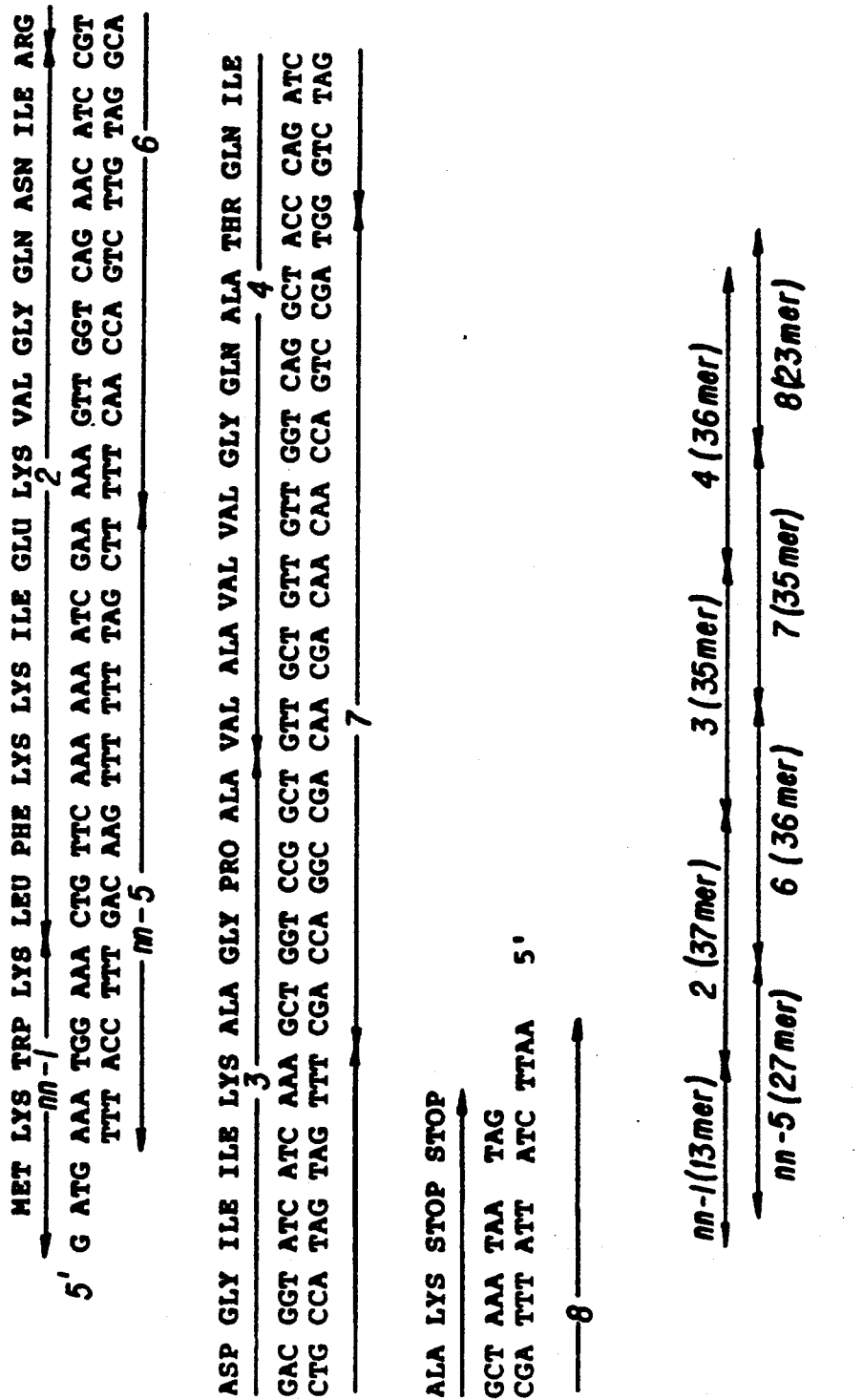
FIG. 6 shows the amino acid and nucleotide sequences of cecropin A, a second chemically synthesized gene used for expression in E. coli.

2. A new CA gene fragment (see FIG. 6) was constructed using the same procedure as described in Example 1, Step B, except that the two DNA fragments No. 1 and 5 were replaced with No. nn-1 and nn-5 (sequence shown in FIG. 6) to produce a "GATG" 5' overhang at its N-terminus and an EcoRI site overhanging ATTT at its C-terminus.

3. pBR322 was digested to completion with the endonucleases BamHI and EcoRI. The resulting digestion was halted as described.

4. The BamHI-FokI fragment from Step 1, supra, and the new CA gene from Step 2, supra, were ligated to the larger BamHI-EcoRI fragment of pBR322.

5. The ligated product was digested with endonuclease HindIII to decrease the number of transformants carrying pBR322.

6. The HindIII-treated plasmid was transformed into E. coli MC1061.

7. The colonies which contained plasmids carrying the CA gene fragment were identified by colony hybridization using the synthetic DNA fragment 7 (FIG. 6) as probe. Three independent clones which contained the CA fragment were found in 1,000 colonies. Each of the isolated plasmids was digested with BamHI and EcoRI; a plasmid able to release the correct fragment as designated pl9C. The nucleotide sequence analysis of the CA inserts was performed by the dideoxy chain termination procedure of Sanger et al., PNAS, 74: 5463-6467 (1977), with some modification (Wallace et al., Gene, 16:21-26 (1981)). pl9C contained the correct sequence for the CA gene. The CA gene was placed directly downstream of the araB promoter without any araB coding sequence in between.

B. Construction of pCA0

1. The BamHI-EcoRI fragments of pl9C were excised by digestion with excess amounts of restriction endonuclease EcoRI and BamHI. The plasmids were also digested with PvuI to decrease the chance that the excised fragments would be religated to the plasmid in the next ligation step.

2. The BamHI-EcoRI fragments from Step A.7 were ligated to plasmid pING 1 which had been pretreated with restriction endonuclease BamHI and EcoRI, then digested with restriction endonuclease SmaI to decrease the transformant carrying pING 1.

3. The SmaI-treated plasmid was transformed into E. coli MC1061.

4. The colonies which contain plasmids carrying the CA gene fragment were identified by plasmid characterization. Each of the isolated plasmids was digested with BamHI and EcoRI to check the size of the excised fragment. One plasmid that had the correct size was designated pCA0. The nucleotide sequence analysis of the CA inserts was performed by the dideoxy chain termination procedure. This pCA0 contained the correct sequence for the CA gene. This pCA0 containing the complete araB regulatory gene and CA gene is placed directly after the araB promoter to express the cecropin-A directly, without creating an araB-CA fusion protein.

C. Construction of Plasmid pCA3A-Δ-1

The purpose of this construction is to delete the AvaI-PvuII region from pCA3A in order to eliminate one XmnI site. The deletion is also able to increase the plasmid copy number in E. coli cells.

1. pCA3A was digested with endonuclease AvaI and PvuII and then filled in with the Klenow fragment of DNA polymerase I in the presence of dNTP to produce a blunt end.

2. The plasmid from Step 1. was religated and then digested with AvaI and PvuII to decrease the number of transformants containing original pCA3A.

3. The AvaI, PvuII-treated plasmid was transformed into E. coli MC1061.

4. Colonies which contained plasmids deleted for the AvaI-PvuII region were identified by colony hybridization using the synthetic DNA fragment 5'-TCAT-CAGCGTGGTCG-3' as a probe. Forty-six independent clones with the AvaI-PvuII region deleted were found in fifty colonies. Each of the isolated plasmids was digested with XmnI to check the size of the excised fragments. One of the plasmids that had the correct size was designated pCA3A-Δ-1.

D. Final Assembly of Plasmid pCA3D pl9C contains the wild-type cecropin-A sequence but lacks a convenient restriction site at its N-terminus to create a protein fusion with araB.

pCA3A has a deletion of two base pairs occurring near the C-terminus of the CA gene, causing it to produce a mutant araB-CA fused protein.

These two plasmids were recombined to construct a plasmid that had the wild-type CA gene fused to araB and produce an araB-CA fused protein.

The construction scheme is shown in FIG. 5.

1. Plasmid pl9C (1 ug) was digested to completion with the endonuclease XmnI; the resulting digestion was halted by heating at 65° C. for 10 min.

2. Plasmid pCA3A-Δ-1 (0.1 ug) was digested to completion with the endonuclease XmnI, the resulting digestion halted by heating at 65° C. for 10 min.

3. DNA from steps D.1 and D.2 were mixed and ligated.

4. The ligated product was digested with PvuII to decrease the transformants carrying pl9C.

5. The PvuII-treated plasmid was transformed into E. coli MC1061.

6. The colonies which contained plasmids carrying the wild-type araB-CA gene and able to produce an araB-CA fused protein were identified by DNA sequence analysis, as previously described. Among seven colonies analyzed, one containing the wild-type sequence was obtained, and designated pCA3D.

TABLE III

Amino Acid Composition of Wild-Type Cecropin-A Produced by pCA3D in E. coli

| Amino Acid | Experimental Values | Expected Values |
|---|---|---|
| Asp | 2.2 | 2 |
| Thr | 1.0 | 1 |
| Glu | 4.1 | 4 |
| Pro | 1.1 | 1 |
| Gly | 4.4 | 4 |
| Ala | 5.2 | 5 |
| Val | 3.4 | 4 |
| Ile | 4.3 | 5 |
| Leu | 0.7 | 1 |
| Phe | 1.1 | 1 |
| Lys | 7.3 | 7 |
| Arg | 1.0 | 1 |
| Trp | ND | 1 |
| Ser | 0.3 | 0 |
| Cys | 0 | 0 |
| Met | 0 | 0 |

TABLE III-continued

Amino Acid Composition of
Wild-Type Cecropin-A Produced by pCA3D in E. coli

| Amino Acid | Experimental Values | Expected Values |
|---|---|---|
| Tyr | 0 | 0 |
| His | 0 | 0 |

N.D. = not determined.

The nucleic acid and amino acid sequence are shown in FIG. 7.

EXAMPLE 4

Assay of Bactericidal Activity

Agar plates (8 cm in diameter) were prepared with 6 ml of TYE medium containing about $10^7$ viable cells of test organism. Wells, 2 mm diameter, were punched in the plates. The test material was dissolved in 50 mM phosphate buffer (pH 6.6) and 3 ul was applied to each well. The diameters of the inhibition zones, or halos, around the wells were measured after overnight incubation at 25° C. To determine a standard of halo formation, CA 1-33 protein was used. 1 ug and 3 ug of CA 1-33 in well applications caused halos with diameters of 8 mm and 11 mm respectively, on media infused with E. coli strain JF568. 10 ug and 30 ug of cyanogen bromide-digested pCA3A araB-CA fusion protein caused halos with diameters 7 mm and 18 mm respectively.

Cyanogen bromide-digested fusion protein fractionated by HPLC was also applied to this assay. Various peaks were tested, and one specific peak was shown to be bioactive. Other bacterial and yeast strains were also tested in this assay. Cyanogen bromide-digested and undigested fusion protein samples were applied in the amounts described above in the testing of E. coli strain JF568, and the resulting halo diameters were measured.

Results are shown for all cecropins obtained in Table IV.

TABLE IV

Bioactivity of CNBr-digested pCA3A, pCA3B, pCA3D
fusion protein isolates (5 ug) and ampicillin (750
ng) on various bacterial strains, as measured by
halo activity.

| Bacterial Strain | Halo Activity in Millimeters | | | |
|---|---|---|---|---|
| | pCA3A[Y] | pCA3B[Y] | pCA3D* | Ampicillin |
| Staphylococcus aureus | NE | NE | NE | 11.5 |
| Streptococcus faecalis | NE | NE | NE | 7.0 |
| Salmonella derby | 5.0 | 5.0 | 5.0 | 6.0 |
| Pseudomonas PS-9 | 2.0 | 2.25 | 2.0 | NE |
| Klebsiella peumoniae | 4.5 | 4.0 | 4.5 | NE |
| Erwinia carotovora EC | 5.0 | 4.5 | 4.75 | 6.5 |
| Streptococcus pyogenes | NE | NE | NE | 12.5 |
| Xenohabdus nematophillus | 3.5 | 3.0 | 2.75 | 12.5 |
| Serratia marcesens | 1.0 | 1.0 | 1.0 | NE |
| E. coli 5506 | 5.0 | 4.5 | 5.0 | 4.5 |
| E. coli 5506 DR | 7.0 | 7.0 | 6.5 | 4.5 |

*Wild
[Y]Mutants
NE No halo activity

EXAMPLE 5

Fermentative Production of Cecropin and of Tumor Growth Factor

This Example describes the fermentation production of alpha-TGF (tumor growth factor) and of cecropin under the control of araB promoter in E. coli.

The E. coli strain MC1061 contains plasmid-borne araB promoter regulating araB-alpha-TGF (pTGF58) or araB-cecropin (pCA3D) fusion gene. The cultures were grown at 37° C., 250 rpm in 100 ml of TYE culture medium containing ampicillin (0.1 gm/l). The cultures were grown until late exponential phase, approximately 200 Klett units; red filter. The cultures were then transferred to a four liter baffled shake flask containing 900 ml fresh TYE medium. Incubation continued for three more hours prior to inoculation into 9 liters of production medium. The production medium comprises the ingredients listed in Table V:

TABLE V

| Base Medium | | Additives | |
|---|---|---|---|
| Ingredients | Level (g/liter) | Ingredients | Level (g/liter) |
| casein hydrolysate | 30 | glycerol | 16 |
| yeast extract | 1 | $CaCl_2:2H_2O$ | 0.022 |
| $KH_2PO_4$ | 3 | $MgSO_4:7H_2O$ | 0.25 |
| $Na_2HPO_4$ | 6 | thiamine-HCl | 0.01 |
| NaCl | 0.5 | ampicillin | 0.1 |
| $NH_4Cl$ | 4 | | |

Initially, the production fermentation conditions were set at 37° C., 800 rpm, and 1 vvm (volume of vessel per minute). As the dissolved oxygen was consumed during the growth time, both agitation and aeration rates were increased accordingly to maintain a minimum dissolved oxygen (D.O.) at 30%. The pH of this medium was consistently self-adjusted at 6.5-6.8, optimum for E. coli growth, such that acid and base control of the medium pH became unnecessary. Approximately four hours following inoculation into the production medium, cell density reach an $O.D._{600}$ of 10 when L-arabinose (50 g) was added to induce the synthesis of cecropin fusion protein. To further ensure the stability of the expression vector, 1 g of ampicillin was supplemented to the broth at an $O.D._{600}$ of 20.

Both alpha-TGF and cecropin-araB fusion proteins were localized only in the insoluble fraction of the E. coli cells. Microscopic examination showed insoluble inclusion bodies were formed inside the cells one hour following induction and were stably maintained throughout the fermentation. More than 95% of the cells contained at least one inclusion body which enlarged rapidly as the cell density kept increasing. The yield of cell mass was 13.1 g (dry weight) per liter. From the cell mass, approximately 30% was the fusion protein.

EXAMPLE 6

Figure 8:
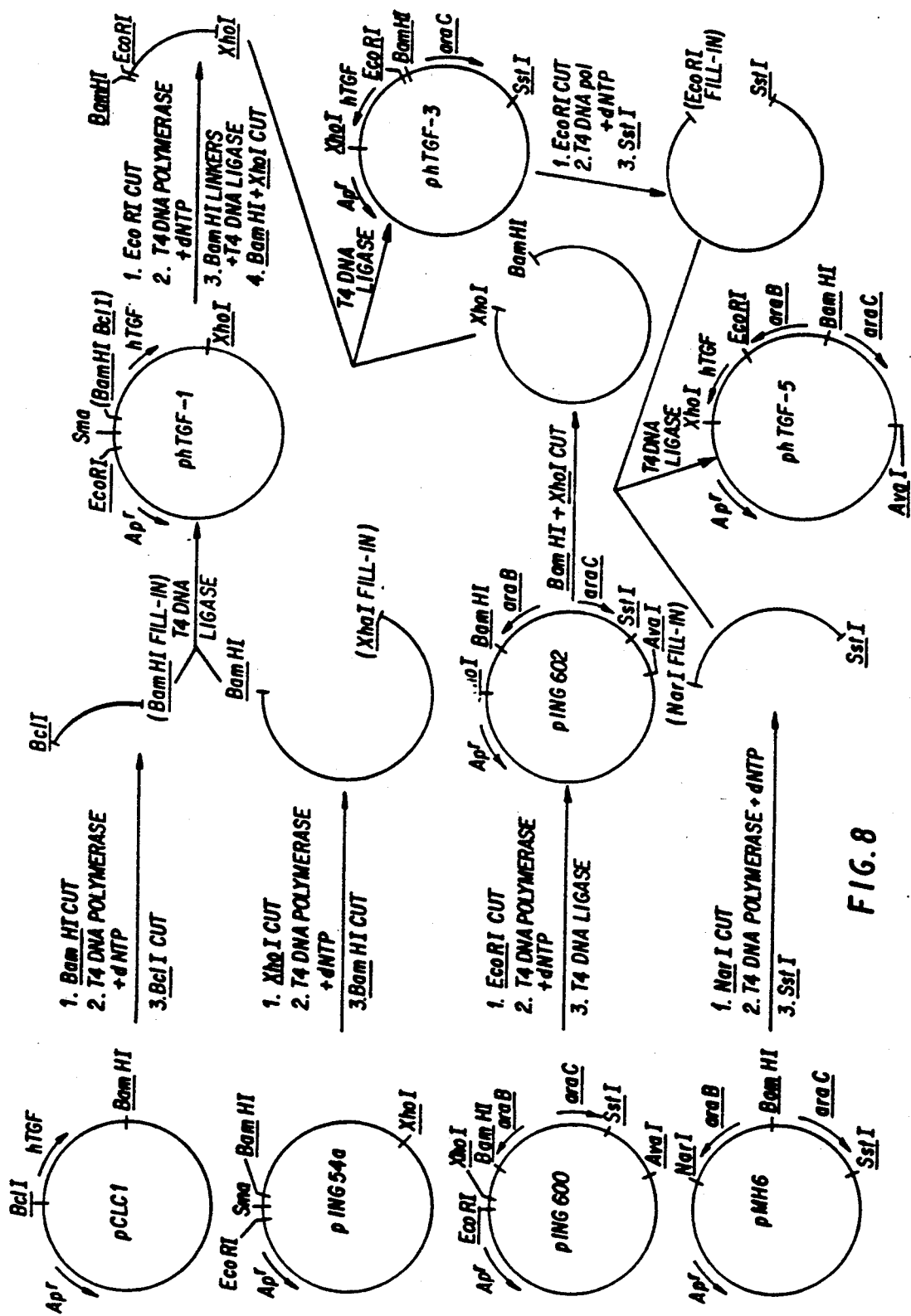
FIG. 8 shows the construction of the plasmid phTGF5 containing an araB-hTGF fusion.

Construction Of E. coli Vector In Which Expression Of araB-hTGF Fusion Protein Is Under Regulation of S. typhimurium araB Promoter The araB promoter is positively regulated by the araC gene product. L-arabinose interacts with the araC protein to form an activator required for expression of the araB promoter. A plasmid which contains the S. typhimurium araB and araC genes was used to construct the araB-hTGF (human tumor growth factor alpha)

expression vector. The strategy of plasmid construction is shown in FIG. 8. The final plasmid phTGF5 contains an araB-hTGF fusion which codes for a protein of 548 amino acids. E. coli strain MC1061 containing phTGF5 was grown in minimal glycerol (1%) medium supplemented with casein hydrolysate (0.5%) and thiamine (1 ug/ml). When the density of the culture reached an A600=0.2, L-arabinose was added to 1% and incubation continued for five hours before the culture was harvested. A 55 KDal protein which represents approximately 10% of the total cellular protein was detected by SDS-PAGE.

EXAMPLE 7

Transcription Terminator 3' Added to the araB-hTGF gene

Figure 9:
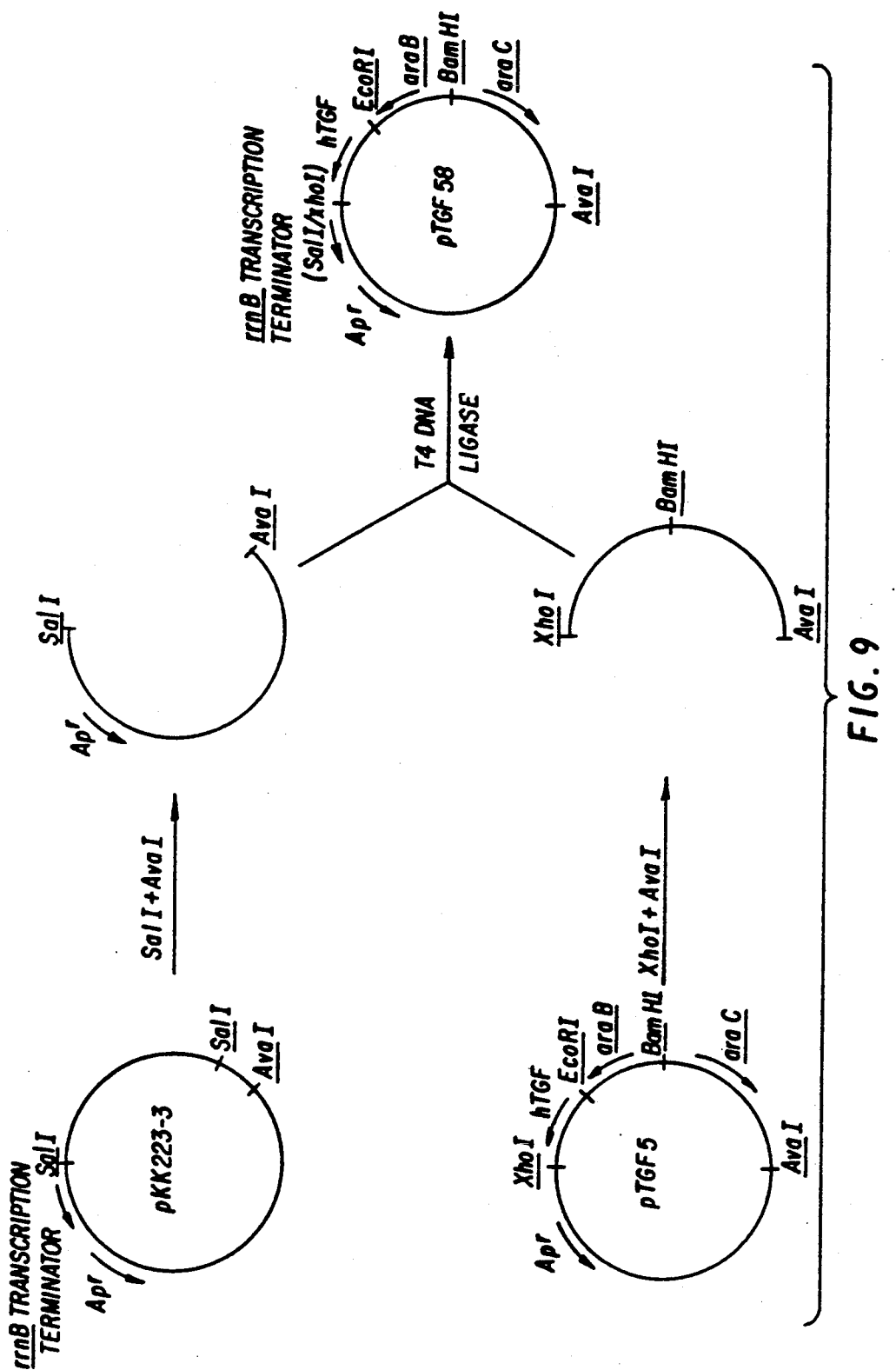
FIG. 9 shows the construction of the plasmid pTGF58.

A transcription terminator is a DNA sequence which causes RNA polymerase to stop transcription. Placement of a transcription terminator at the 3' end of the araB-hTGF gene will prevent the expression of the undesired gene product(s) downstream from the transcription terminator. The strategy of plasmid construction as shown in FIG. 9. The final plasmid phTGF58 contains an E. coli rrnB gene transcription terminator inserted at the 3'-end of the araB-hTGF gene. When the partially purified araB-hTGF proteins isolated from E. coli strain MC1061 containing either phTGF58 or phTGF5 (the parent plasmid) were compared after electrophoresis on SDS-polyacrylamide gel, a major contaminant protein, beta-lactamase, was significantly reduced in phTGF58-containing cells.

EXAMPLE 8

The araB Promoter and Calcitonin

A. The human calcitonin gene (hCT)

Calcitonin or thyrocalcitonin (CT) is the name given to the hypocalcemic hormone secreted from the thyroid. CT decreases bone resorptive activity. CT also acts on kidneys to stimulate increased urinary calcium and phosphate clearance. The rapid release of CT in response to blood calcium elevations suggests that the main purpose of CT is to protect higher animals from acute hypercalcemic episodes. Research in CT is examining its use in the control of Paget's disease, a problem of accelerated bone remodeling.

The sequence for the human gene for calcitonin is as follows (Craig et al., Nature, 295: 345-347 (1982)):

Cys Gly Asn Leu Ser Thr Cys Met Leu Gly
TGC GGT AAT CTG AGT ACT TGC ATC CTG GGC

Thr Tyr Thr Gln Asp Phe Asn Lys Phe His
ACA TAC ACG CAG GAC TTC AAC AAG TTT CAC

Thr Phe Pro Gln Thr Ala Ile Gly Val Gly
ACG TTC CCC CAA ACT GCA ATT GGG GTT GGA

Ala Pro Gly
GCA CCT GGA

Figure 10:
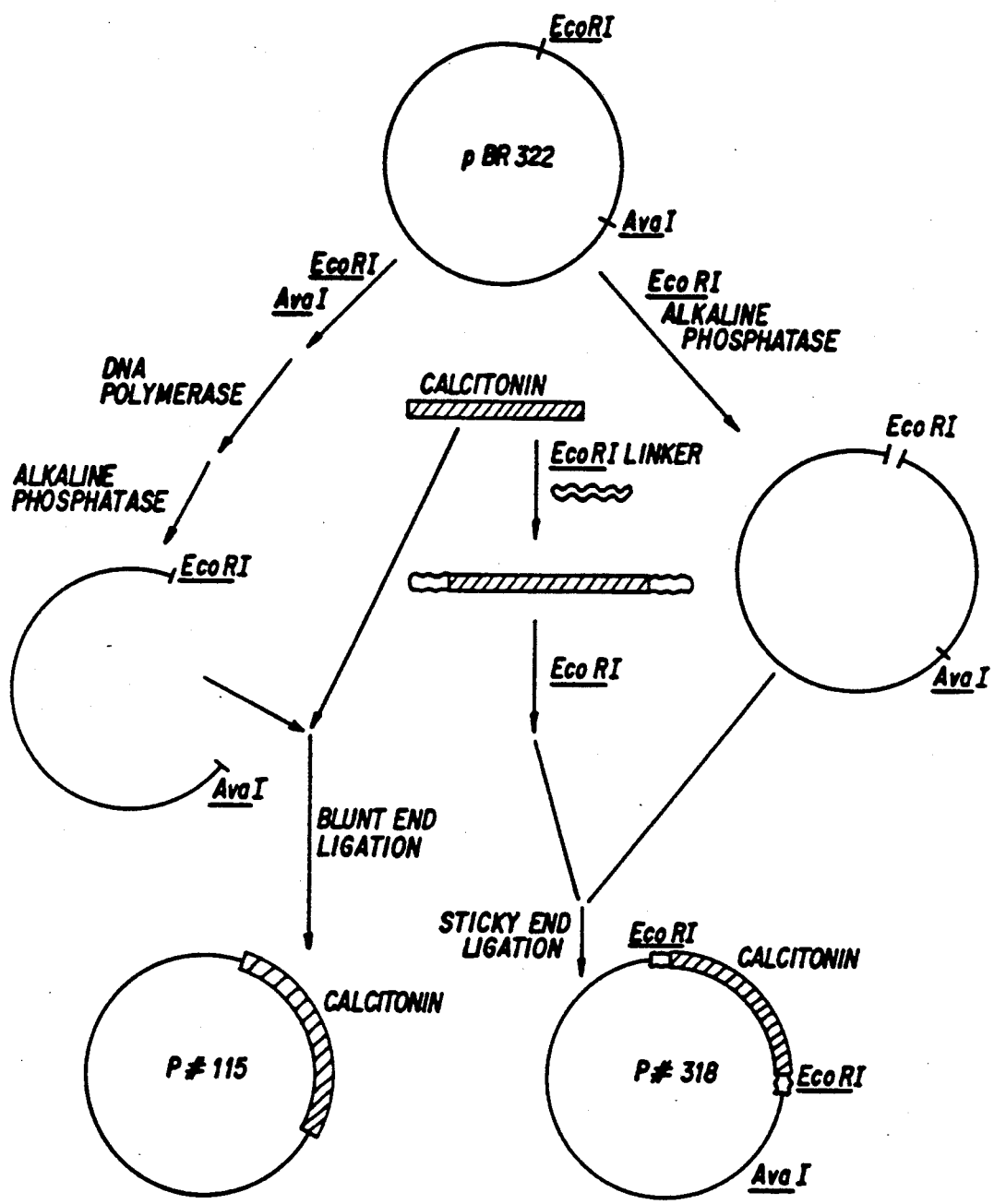
FIG. 10 shows the construction of two plasmids, p115 and p318, carrying a human synthetic calcitonin gene.
Figure 11:
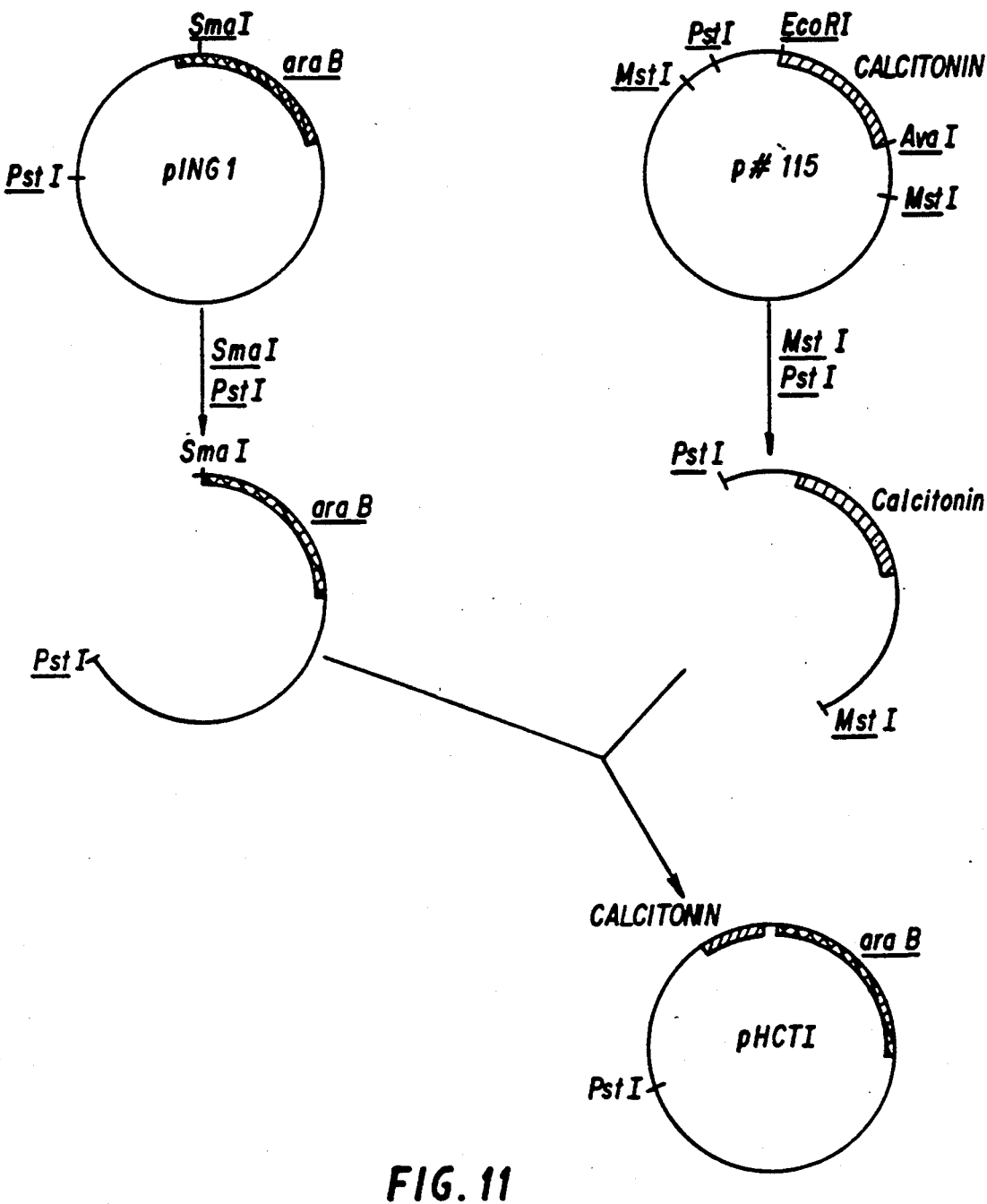
FIG. 11 shows the construction of a plasmid, pHCT1, containing the gene for the fused polypeptide ribulokinase-human calcitonin (hCT).

B. Construction of a plasmid carrying an inducible regulon, the araB structural gene and the hCT Gene Plasmid p115, its construction shown in FIG. 10, contains the correct calcitonin gene sequence. The plasmid was digested with endonucleases MstI and PstI to excise the calcitonin gene, as shown in FIG. 11. The excised fragment was ligated to a plasmid carrying the araB structural gene (plasmid pING1. see FIG. 12).

Figure 12:
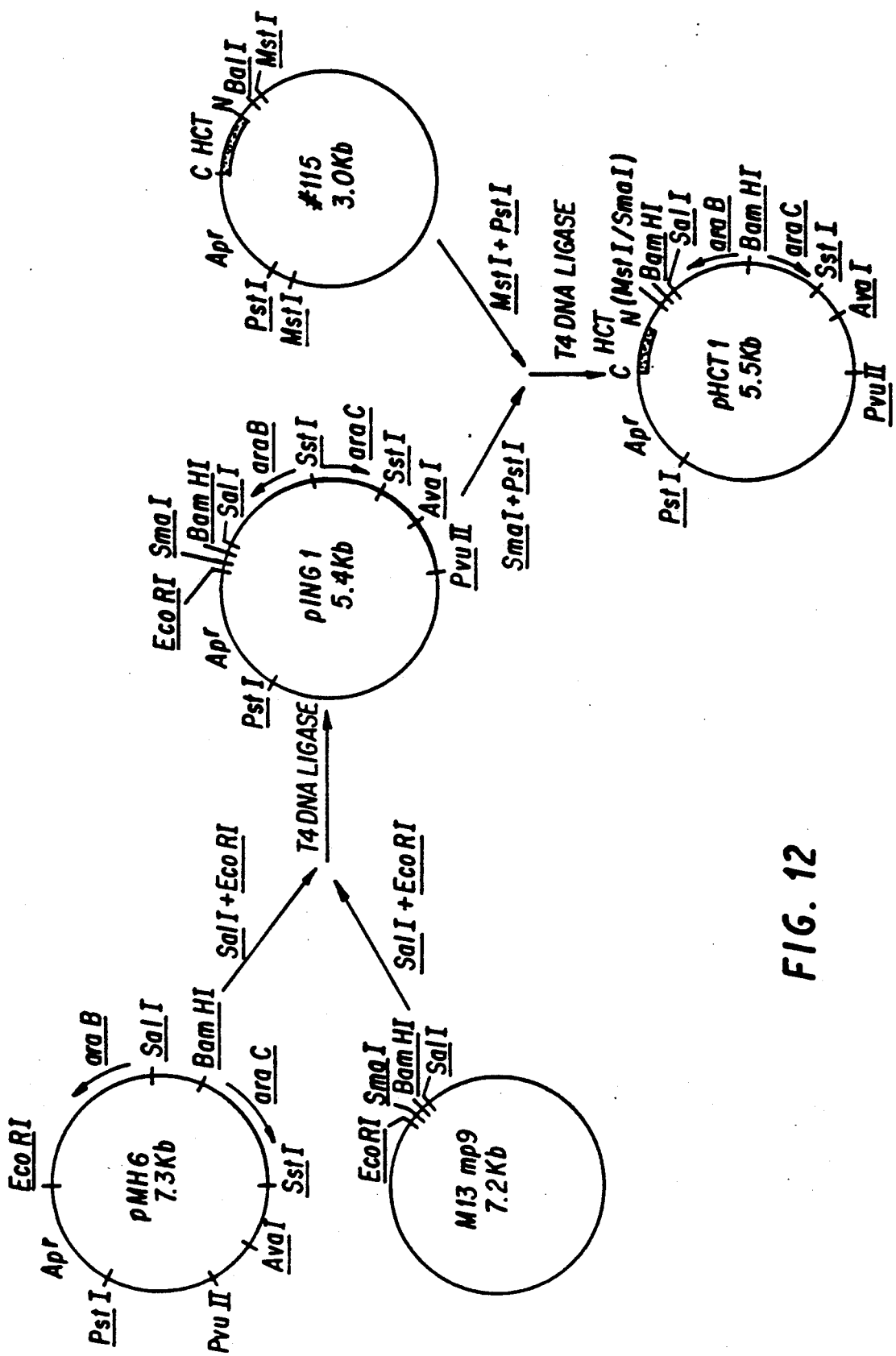
FIG. 12 shows the construction of plasmid pING1, used as a vehicle for cloning and expression of calcitonin-peptide genes; pING1 carries araB and araC genes.

Plasmid pMH6 (Horwitz et al., Gene, 14: 309-319 (1981)) which contains intact araC and araB was used as starting material for construction of pING1. The construction scheme is shown in FIG. 12. The plasmid pMH6 was digested with restriction endonuclease FcoRI and SalI, which cut in araB and araA gene, respectively, and the 1.9 kb SalI-EcoRI fragment was replaced by a 16 base-pair SalI-EcoRI fragment from M13 mp9 (Vieira and Messing, Gene, 19: 259-268 (1982)) to generate pING1. The reading frame of the araB gene was determined by fusion of the lacZ gene to the EcoRI site in pING1. Since both restriction endonuclease SmaI and MstI create blunt end fragments, the 760 base-pair fragment of pING1 was then replaced by a MstI-PstI fragment from plasmid #115 to generate phCT1. Plasmid #115 has the chemically synthesized hCT gene located in the MstI-PstI fragment. The joining of the MstI and SmaI end fused the hCT gene to the araB gene making an araB-hCT protein fusion.

C. Growth of E. coli cells containing phCT1

Transformed E. coli cells containing phCT1 were grown at 37° C., with shaking, to a density of $10^8-10^9$/ml, and the synthesis of the araB-calcitonin fused protein was induced by the addition of L-arabinose (1% wt/vol) during additional growth for 1-6 hours. The harvested cells were sonicated (5 sec, 3 times) and the concentration of araB-calcitonin was assayed by an ELISA procedure using anti-hCT antibodies.

Although the foregoing invention has been described in some detail by way of illustration and example for purposes of clarity of understanding, it will be obvious that certain changes and modifications may be practiced within the scope of the invention, as limited by the scope of the appended claims.

What is new and intended to be covered by Letters Patent of the United States is:

1. A genetic construct which comprises a first genetic sequence coding for a polypeptide which is capable of suppressing the bactericidal effect of the resulting fusion protein towards an otherwise cecropin-sensitive bacterium operably linked to a second genetic sequence coding for cecropin.

2. The genetic construct of claim 1 wherein said polypeptide is a leading polypeptide.

3. The genetic construct of claim 1 wherein said genetic sequence coding for said polypeptide comprises between about 300 and 5,000 base pairs.

4. A vehicle replicable in a given host comprising the genetic construct of claim 1.

5. The vehicle of claim 4 which is expressible in a bacterium.

6. The vehicle of claim 4 wherein said cecropin is A, B or D.

7. The genetic construct of claim 1 which also includes an inducible promoter in operable linkage therewith.

8. The genetic construct of any one of claims 1 or 7, wherein said genetic sequence coding for cecropin is a synthetic sequence.

9. The method of claim 8 which further includes a step of cleaving the protein conjugate into cecropin and said different polypeptide.

10. The genetic construct of any one of claims 1 or 7, wherein said cecropin is cecropin A, B or D.

11. A host transformed with the genetic construct of any one of claims 1 or 7.

12. The host of claim 11 which is a cecropin-sensitive bacterium.

13. The host of claim 11 wherein said cecropin is A, B or D.

14. A cecropin-sensitive host transformed with a vehicle expressible therein, said vehicle carrying a genetic sequence coding for cecropin operably linked to a genetic sequence coding for a polypeptide capable of suppressing the bactericidal effect of said cecropin towards said host in the resulting expression fusion product.

15. A method of producing cecropin by microbial techniques which comprises:
    operably linking a first genetic sequence coding for cecropin with a second genetic sequence coding for a different polypeptide to form a fused gene;
    transforming said fused gene into a cecropin susceptible host;
    culturing said transformed host, whereby a protein conjugate non-toxic to said host is produced; and
    subsequently recovering cecropin from said protein conjugate.

* * * * *

UNITED STATES PATENT AND TRADEMARK OFFICE
CERTIFICATE OF CORRECTION

PATENT NO. : 5,206,154
DATED : April 27, 1993
INVENTOR(S) : LAI et al

It is certified that error appears in the above-indentified patent and that said Letters Patent is hereby corrected as shown below:

On the title page: Item [56] Related U.S. Appl. Data:

line 2, after "which is a" please insert --continuation of Ser. No. 797,472, Nov. 13, 1985, abandoned, which is a --;

line 3, please change "645,309" to --695,309--.

This application is a division of application serial no. 07/474,304 now U.S. Pat. No. 5,028,530 filed February 5, 1990 which is a continuation in part of capplication serial no. 07/645,309 filed January 28, 1985, which is now abandoned.

Signed and Sealed this

Eleventh Day of October, 1994

Attest:

BRUCE LEHMAN

*Attesting Officer*       *Commissioner of Patents and Trademarks*